(12) United States Patent
Pouwels et al.

(10) Patent No.: US 10,493,147 B2
(45) Date of Patent: Dec. 3, 2019

(54) BROAD-SPECTRUM VACCINE AGAINST AVIAN REOVIRUS

(71) Applicant: Intervet Inc., Madison, NJ (US)

(72) Inventors: Henk Pouwels, Gael (BE); Saskia van de Zande, Siebengewald (NL)

(73) Assignee: Intervet Inc., Madison, NJ (US)

( * ) Notice: Subject to any disclaimer, the term of this patent is extended or adjusted under 35 U.S.C. 154(b) by 48 days.

(21) Appl. No.: 15/515,617

(22) PCT Filed: Oct. 2, 2015

(86) PCT No.: PCT/EP2015/072810
§ 371 (c)(1),
(2) Date: Mar. 30, 2017

(87) PCT Pub. No.: WO2016/050961
PCT Pub. Date: Apr. 7, 2016

(65) Prior Publication Data
US 2018/0326043 A1    Nov. 15, 2018

(30) Foreign Application Priority Data

Oct. 3, 2014   (EP) .................................... 14187650

(51) Int. Cl.
*A61K 39/15*   (2006.01)
*A61P 31/14*   (2006.01)
*A61K 39/12*   (2006.01)
*A61K 39/00*   (2006.01)

(52) U.S. Cl.
CPC .............. *A61K 39/15* (2013.01); *A61K 39/12* (2013.01); *A61P 31/14* (2018.01); *A61K 2039/5252* (2013.01); *A61K 2039/552* (2013.01); *A61K 2039/55566* (2013.01); *A61K 2039/58* (2013.01); *A61K 2039/70* (2013.01); *C12N 2720/12034* (2013.01)

(58) Field of Classification Search
None
See application file for complete search history.

(56) References Cited

U.S. PATENT DOCUMENTS 6,951,650 B1    10/2005   Van
2018/0326044 A1*  11/2018   Carter ................... A61K 39/12

FOREIGN PATENT DOCUMENTS

| WO | WO 2004/032959 | * | 4/2004 |
| WO | 2004032959 A3 |  | 6/2004 |
| WO | WO 2008/076518 | * | 6/2008 |

OTHER PUBLICATIONS

Sellers (Veterinary Microbiology. 2017; 206: 152-156).*
Palomino-Tapia et al. (Vaccine. 2018; 522: 138-146).*
Meanger et al. (Avian Pathology. 1995; 24: 121-134).*
(Continued)

*Primary Examiner* — Shanon A. Foley

(57) ABSTRACT

A broad-spectrum vaccine against avian Reovirus is disclosed, which is effective in reducing the infection of avian Reovirus in an avian target. The vaccine comprises antigenic material derived from avian Reovirus of two genotype groups: 1 and 4, as defined herein. This vaccine is effective against all avian Reoviruses, homologous or heterologous to the vaccine, including recent virulent break-through strains.

Figure 1:
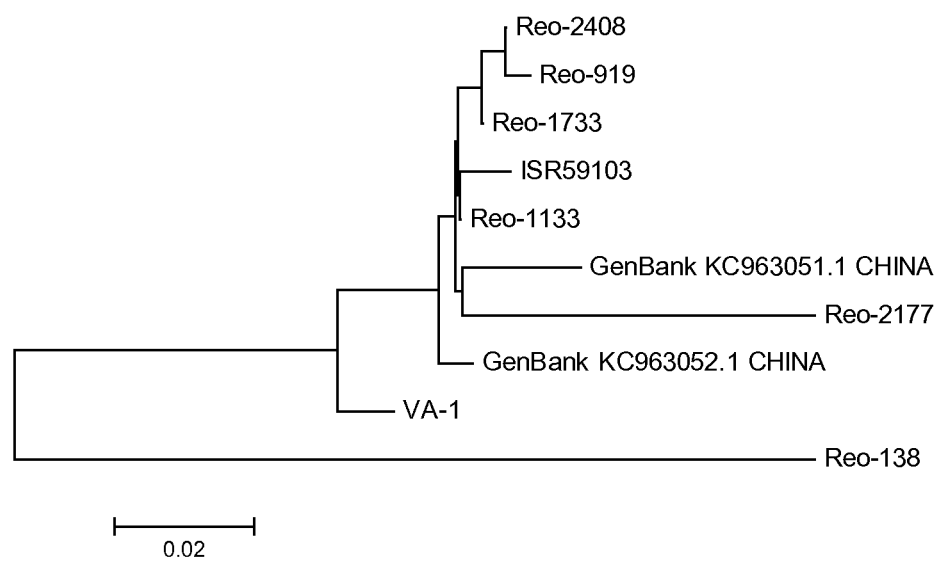

9 Claims, 6 Drawing Sheets
Specification includes a Sequence Listing.

(56) References Cited

OTHER PUBLICATIONS

Alignment of SEQ ID 1 with Geneseq database acc No. BDV61355 by Carter in WO2017066484 on Jun. 2017.*
Alignment of SEQ ID 4 with UniProt database acc No. Q9DPB3_9REOV by Liu et al. Mar. 2008.*
Alignment of SEQ ID 1 with Geneseq db acc No. AXF62208 in WO2009093251 by Pitkovski et al Sep. 2009.*
Alignment of SEQ ID 1 with UniProt db acc No. U4DBR7_9REOV Troxler et al Dec. 2013.*
Alignment of SEQ ID 4 with UniProt db acc No. O80V09_9REOV by Kant et al. Jun. 2002.*
Alignment of SEQ ID 4 with Geneseq db acc No. ARY99771 by Sellers in WO2008076518 Jun. 2008.*
International Search Report PCT/EP2015/072810 dated Jan. 5, 2016, 14 pages.
J. Michael Day, The diversity of the orthoreoviruses: Molecular taxonomy and phylogentic divides, Infection, Genetics and Evolution, 2009, pp. 390-400, 9.
Kant, A. et al., Classification of Dutch and German avian reoviruses by sequencing the *C protein, Vet. Res., 2003, pp. 203-212, vol. 34.
Liu, H.J.et al., Molecular evolution of Avian Reovirus: evidence for genetic diversity and reassortment of the S-class genome segments and multiple cocirculating lineages, Virology, 2003, pp. 336-349, vol. 314.
Lublin, A. et al., Wide-range protection against avian reovirus conferred by vaccination with representatives of four defined genotypes, Vaccine, 2011, pp. 8683-8688, vol. 29.
Meanger, J. et al., Type-specific antigenicity of avian reoviruses, Avian Pathology, 1995, pp. 121-134, vol. 24.
Moreira, F.A. et al., Presumptive reovirus infection in broiler breeders, American Journal of Animal and Veterinary Sciences, 2014, pp. 53-55, Published online (http://www.thescipub.com/ajavs.toc), 9 (1).
Troxler, S. et al., Identification of a new reovirus causig substantial losses in broiler production in France, despite routine vaccination of breeders, Veterinary Record, published online May 1, 2013, p. 556 and further, vol. 172.
Wood, G.W. et al., Observations on the ability of avian reovirus vaccination of hens to protect their progeny against the effects of challenge with homologous and heterologous strains, Comp. Path., 1986, pp. 125-129, vol. 96.

* cited by examiner

```
                        SEQUENCE LISTING

<160> NUMBER OF SEQ ID NOS: 20

<210> SEQ ID NO 1
<211> LENGTH: 315
<212> TYPE: PRT
<213> ORGANISM: Avian orthoreovirus
<220> FEATURE:
<221> NAME/KEY: misc_feature
<222> LOCATION: (168)..(168)
<223> OTHER INFORMATION: Xaa can be any naturally occurring amino acid

<400> SEQUENCE: 1

Met Ala Gly Leu Asn Pro Leu Gln Arg Arg Glu Val Val Ser Leu Ile
1               5                   10                  15

Leu Ser Leu Thr Ser Asn Val Thr Thr Asn Pro Gly Asp Leu Lys Ser
            20                  25                  30

Ile His Glu Arg Leu Thr Ser Leu Glu Ala Ser Thr Glu Ser Leu His
        35                  40                  45

Gln Ser Val Ser Gly Met Ser Ala Thr Leu Ser Gly Leu Ser Ala Asp
    50                  55                  60

Leu Gln Asp Thr Thr Arg Thr Leu Asp Asp Val Thr Val Thr Leu Asn
65                  70                  75                  80

Gly Leu Ser Ala Thr Ile Ala Ala Leu Gln Asn Ser Leu Thr Thr Leu
                85                  90                  95

Ser Ala Thr Val Asp Glu Leu Ala Asn Thr Ser Ser Ala His Ser Gly
            100                 105                 110

Met Leu Ser Ser Leu Gln Thr Ala Val Asn Gly Asn Ser Ser Asp Ile
        115                 120                 125

Ala Asn Leu Arg Ser Asp Val Ser Ala Asn Gly Leu Asn Ile Thr Asp
    130                 135                 140

Leu Gln Asn Arg Ile Lys Ser Leu Glu Ser Asp Thr Ser His Cys Leu
145                 150                 155                 160

Ser Phe Ser Pro Pro Leu Ser Xaa Ala Asp Gly Val Val Ser Leu Asp
                165                 170                 175

Met Asp Pro Tyr Phe Cys Ser Gln Arg Val Ser Leu Thr Ser Tyr Ser
            180                 185                 190

Ala Glu Ala Gln Leu Met Gln Phe Gln Trp Val Ala Lys Gly Thr Ser
```

```
            195                 200                 205
Gly Ser Ser Asp Thr Ile Asp Met Ile Val Asn Ala His Cys His Gly
    210                 215                 220

Arg Arg Thr Asp Tyr Ile Met Ser Ser Thr Gly Ser Leu Thr Val Thr
225                 230                 235                 240

Ser Asn Ala Val Ser Leu Thr Phe Asp Leu Ser Tyr Ile Thr Asn Met
                245                 250                 255

Pro Ser Asp Leu Ser Arg Leu Ile Pro Ser Ala Gly Phe Gln Val Ala
            260                 265                 270

Ser Phe Pro Val Asp Val Ser Phe Thr Arg Glu Ser Thr His Thr
    275                 280                 285

Tyr Gln Ser Tyr Gly Ala Tyr Ser Ser Ala Arg Val Phe Thr Ile Thr
    290                 295                 300

Phe Pro Thr Gly Gly Asn Gly Thr Ser Asn Ile
305                 310                 315

<210> SEQ ID NO 2
<211> LENGTH: 309
<212> TYPE: PRT
<213> ORGANISM: Avian orthoreovirus
<220> FEATURE:
<221> NAME/KEY: misc_feature
<222> LOCATION: (137)..(137)
<223> OTHER INFORMATION: Xaa can be any naturally occurring amino acid

<400> SEQUENCE: 2

Met Ala Gly Leu Thr Pro Ser Gln Arg Arg Glu Val Val Gly Leu Ile
1               5                   10                  15

Leu Ser Leu Thr Ser Ser Ala Thr Thr Ser Cys Gly Asp Leu Thr Ala
                20                  25                  30

Ile Asn Glu Arg Leu Leu Lys Leu Asp Ser Ser Val Glu Ser Leu Thr
            35                  40                  45

Ile Ser Val Gly Asp Leu Ser Arg Arg Phe Ser Glu Leu Glu Val Asp
    50                  55                  60

Leu Gln Asn Val Asp Ser Ser Leu Arg Gln Leu Thr Ser Ser Leu Asn
65                  70                  75                  80

Thr Leu Ser Glu Glu Val Arg Gln Leu Arg Ser Ala Val Ser Asp Asn
                85                  90                  95

Thr Val Ser Ile Ser Gly Leu Ser Ala Thr Val Ala Asp His Gln Gln
            100                 105                 110

Val Leu Thr Asp Leu Gln Thr Ser Val Asn Ala Asn Val Thr Asp Ile
    115                 120                 125

Thr Asn Leu Lys Gly Ser Val Thr Xaa Leu Ser Leu Thr Val Ala Asp
130                 135                 140

Leu Glu Lys Arg Leu Lys Val Val Glu Ser Gly Ser Ser Ser Thr Leu
145                 150                 155                 160

Glu Phe Thr Ser Pro Leu Ser Leu Thr Asn Gly Val Val Ser Leu Asn
                165                 170                 175

Met Asp Pro Tyr Phe Cys Ser Asp Asn His Ala Leu Thr Ser Tyr Ser
            180                 185                 190

Ser Asp Ala Gln Leu Met Gln Phe Gln Trp Leu Ala Arg Gly Asp Asp
    195                 200                 205

Gly Ser Ser Asp Ser Val Glu Met Leu Val Asn Ala His Cys His Gly
    210                 215                 220

Arg Arg Thr Asp Tyr Met Met Ser Thr Thr Glu Asn Leu Thr Val Thr
225                 230                 235                 240
```

```
Gly Asn Ser Thr Ser Leu Val Phe Ser Leu Glu Tyr Ile Thr Lys Pro
            245                 250                 255

Pro Ser Asp Met Ser Arg Leu Val Pro Arg Ala Gly Phe Gln Ala Ala
            260                 265                 270

Ser Phe Pro Val Asp Val Ser Phe Thr Arg Asp Thr Ala Thr His Ala
            275                 280                 285

Tyr Gln Val Tyr Gly Ala Phe Thr Ser Pro Arg Val Phe Lys Ile Thr
            290                 295                 300

Phe Leu Thr Gly Gly
305

<210> SEQ ID NO 3
<211> LENGTH: 313
<212> TYPE: PRT
<213> ORGANISM: Avian orthoreovirus

<400> SEQUENCE: 3

Met Ala Gly Leu Thr Pro Ser Gln Arg Arg Glu Val Val Gly Leu Ile
1               5                   10                  15

Leu Ser Leu Thr Ser Asn Ala Ser Ile Asn Pro Gly Asp Leu Ala Pro
            20                  25                  30

Ile Tyr Ser Arg Leu Thr Ala Leu Glu Val Ala Arg Asp Glu Leu Asn
            35                  40                  45

Lys Ser Leu Thr Glu Leu Ser Ser Ala Met Ser Ala Phe Ser Ile Arg
        50                  55                  60

Phe Asp Asp Ala Leu Met Lys Leu Asn Ser Val Thr Ala Asp Leu Thr
65                  70                  75                  80

Val Ile Lys Ser Asp Ile Ser Thr Leu Asn Ser Ser Val Ser Ala Val
            85                  90                  95

Thr Ser Ser Thr Ala Gly Leu Ser Gln Ser Val Ser Ser His Glu Ser
            100                 105                 110

Gln Leu Ala Thr Leu Ser Ser Ser Leu Thr Thr Leu Ser Ser Gln Met
            115                 120                 125

Ala Ala Leu Gln Arg Asp Val Ser Thr Ser Glu Leu Lys Leu Thr Asp
        130                 135                 140

Leu Gln His Arg Val Thr Ala Leu Glu Ser Ser Gly Gly Ala Ser Leu
145                 150                 155                 160

Gln Phe Leu Pro Pro Leu Lys Thr Asp Gly Thr Ser Val Ser Leu Glu
            165                 170                 175

Leu Asp Pro Tyr Phe Cys Ser Glu Arg His Asn Leu Thr Ser Tyr Ser
            180                 185                 190

Ala Ala Ala Gln Leu Leu Gln Phe Gln Trp Leu Ile Arg Ser Glu Asn
            195                 200                 205

Gly Ala Ser Asp Ser Phe Asp Met Asn Val Val Ala His Cys His Gly
            210                 215                 220

Arg Arg Thr Asp Tyr Leu Met Ser Thr Pro Ser Ser Leu Thr Val Thr
225                 230                 235                 240

Ser Asn Ser Val Ser Leu Val Phe Asp Leu Ser Phe Ile Thr Thr Pro
            245                 250                 255

Gln Val Asp Leu Ala Arg Leu Val Pro Cys His Gly Phe Gln Gln Ala
            260                 265                 270

Thr Phe Pro Val Asp Val Ser Tyr Thr Arg Gly Asp Thr Thr His Ser
            275                 280                 285

Tyr Gln Val Tyr Gly Ser Phe Asp Thr Pro Arg Ile Phe Lys Ile Thr
```

```
                290                 295                 300

Phe Ser Thr Gly Gly Thr Gly Thr Ala
305                 310

<210> SEQ ID NO 4
<211> LENGTH: 315
<212> TYPE: PRT
<213> ORGANISM: Avian orthoreovirus

<400> SEQUENCE: 4

Met Glu Gly Leu Thr Gln Ser Gln Arg Arg Glu Val Val Gly Leu Ile
1               5                   10                  15

Leu Ser Leu Thr Ser Ser Val Thr Thr Ser Thr Gly Asp Leu Ala Gln
            20                  25                  30

Ile Arg Ser Arg Leu Ser Ala Leu Glu Ser Ser Asn Ala Leu Leu Ser
        35                  40                  45

Glu Thr Val Asn Gly Ala Leu Ser Gln Leu Val Ala Leu Ser Ser Arg
    50                  55                  60

Leu Asp Asn Leu Ala Ala Thr Val Ala Asp Gly Gln Leu Glu Leu Arg
65                  70                  75                  80

Ser Leu Thr Thr Asp Val Lys Asn Ile Arg Ser Leu Leu Asp Asp Ile
                85                  90                  95

Ser Thr Thr Val Ala Ser Leu Ser Ala Ser Val His Lys His Asp Leu
            100                 105                 110

Ser Ile Ser Asp Leu Ala Arg Gln Phe Gly Leu Leu Thr Thr Asp Thr
        115                 120                 125

Ala Asn Leu Lys Thr Asp Val Ala Thr Gln Ser Leu Gln Ile Thr Ser
    130                 135                 140

Leu Glu Gln Arg Val Thr Ala Leu Glu Ser Gly Thr Gly Ser Leu Pro
145                 150                 155                 160

Ser Phe Ser Ala Pro Leu Lys Leu Asp Asp Gly Thr Val Ser Leu Asp
                165                 170                 175

Leu Asp Pro Tyr Phe Cys Ser Val Asp His Asn Leu Thr Ser Tyr Ser
            180                 185                 190

Ala Ser Ala Gln Leu Met Gln Phe Gln Trp Leu Val Arg Gly Glu Gly
        195                 200                 205

Gly Ser Ser Asp Ser Ile Asp Met Asn Val Thr Ala His Cys His Gly
    210                 215                 220

Arg Arg Thr Asp Tyr Met Met Ser Thr Thr Gln Ser Leu Thr Val Thr
225                 230                 235                 240

Gly Thr Ser Val Ser Leu Val Phe Asn Leu Asp Thr Leu Ile Thr Ser
                245                 250                 255

Pro Ser Asp Tyr Ser Arg Leu Ile Pro Cys His Gly Phe Gln Gln Ala
            260                 265                 270

Thr Phe Pro Val Asp Leu Ser Phe Lys Arg Asp Glu Val Thr His Ser
        275                 280                 285

Tyr Gln Val Tyr Gly Ser Tyr Ser Thr Pro Arg Val Phe Lys Val Thr
    290                 295                 300

Phe Ser Pro Gly Ala Pro Val Pro Ala Val Ile
305                 310                 315

<210> SEQ ID NO 5
<211> LENGTH: 316
<212> TYPE: PRT
<213> ORGANISM: Avian orthoreovirus
```

<400> SEQUENCE: 5

```
Met Ala Gly Leu Asn Pro Ser Gln Arg Arg Glu Val Val Ser Leu Ile
1               5                   10                  15

Leu Ser Leu Thr Ser Ser Thr Thr Ser Pro Gly Asp Leu Ile Gln
            20                  25                  30

Ile Arg Glu Arg Leu Ser Ala Leu Glu Ser Ala Asn Ala Leu Leu Asn
            35                  40                  45

Glu Ser Val Asn Thr Ala Leu Ser Lys Leu Gly Asp Phe Ser Val Ala
    50                  55                  60

Leu Asp Asn Met Ala Val Asn Val Ala Glu Thr Lys Val Glu Leu Ala
65                  70                  75                  80

Ser Leu Ala Ser Asp Val Gln Ser Leu Arg Thr Ser Leu Asp Ser Thr
                85                  90                  95

Ala Ser Glu Val Ala Ser Leu Ser Leu Leu Val His Gly His Gly Ser
            100                 105                 110

Ser Ile Ser Asp Leu Gln Gln Lys Gly Tyr Ala Leu Ser Gly Glu Val
            115                 120                 125

Asp Asn Leu Lys Ser Ser Val Ser Ser Gln Gly Leu Thr Ile Ser Gly
130                 135                 140

Leu Glu Ser Gln Val Gln Ala Leu Glu Ser Gly Ser Gly Thr Asp Leu
145                 150                 155                 160

Leu Phe Ala Asp Pro Leu Lys Leu Glu Ala Gly Thr Val Ser Leu Asp
                165                 170                 175

Leu Asp Pro Tyr Phe Cys Ser Val Ser Arg Asn Leu Thr Ser Tyr Ser
            180                 185                 190

Ala Ser Ala Gln Leu Met Gln Phe Gln Trp Ser Val Lys Gly Glu Asp
            195                 200                 205

Gly Ala Ala Asn Ser Ile Asp Met Asp Val Asn Ala His Cys His Gly
            210                 215                 220

Pro Arg Thr Asp Tyr Leu Met Ser Thr Lys Gln Ser Leu Thr Val Thr
225                 230                 235                 240

Thr Ser Pro Ala Thr Leu Val Phe Glu Leu Asp Arg Ile Val Thr Leu
                245                 250                 255

Pro Pro Asp Leu Ser Arg Leu Ile Pro Cys His Ala Phe Gln Gln Ala
            260                 265                 270

Thr Phe Pro Val Asp Ile Ser Phe Gln Arg Glu Gly Val Ser His Thr
            275                 280                 285

Tyr Gln Val Tyr Gly Thr Tyr Thr Ser Ser Arg Val Phe Arg Ile Thr
            290                 295                 300

Phe Ser Pro Gly Ser Pro Gly Pro Thr Val Ile Gln
305                 310                 315
```

<210> SEQ ID NO 6
<211> LENGTH: 309
<212> TYPE: PRT
<213> ORGANISM: Avian orthoreovirus

<400> SEQUENCE: 6

```
Met Ala Gly Leu Asn Pro Ser Gln Arg Arg Glu Val Val Ser Leu Ile
1               5                   10                  15

Leu Ser Leu Thr Ser Asn Val Thr Ile Ser His Gly Asp Leu Thr Pro
            20                  25                  30

Ile Tyr Glu Arg Leu Thr Asn Leu Glu Ala Ser Thr Glu Leu Leu His
            35                  40                  45
```

```
Arg Ser Ile Ser Asp Ile Ser Thr Thr Val Ser Asn Ile Ser Ala Asn
    50                  55                  60

Leu Gln Asp Met Thr His Thr Leu Asp Asp Val Thr Ala Asn Leu Asp
65                  70                  75                  80

Gly Leu Arg Thr Thr Val Thr Ala Leu Gln Asp Ser Val Ser Ile Leu
                    85                  90                  95

Ser Thr Asn Val Thr Asp Leu Thr Asn Thr Ser Ser Ala His Ala Ala
                100                 105                 110

Thr Leu Ser Ser Leu Gln Thr Thr Val Asp Glu Asn Ser Thr Ala Ile
                115                 120                 125

Ser Asn Leu Lys Ser Asp Val Ser Ser Asn Gly Leu Ala Ile Thr Asp
130                 135                 140

Leu Gln Asp Arg Val Lys Ser Leu Glu Ser Thr Ala Ser His Gly Leu
145                 150                 155                 160

Ser Phe Ser Pro Pro Leu Ser Val Ala Asp Gly Val Val Ser Leu Asp
                165                 170                 175

Met Asp Pro Tyr Phe Cys Ser Gln Arg Val Ser Leu Thr Ser Tyr Ser
                180                 185                 190

Ala Glu Ala Gln Leu Met Gln Phe Arg Trp Met Ala Arg Gly Thr Asn
                195                 200                 205

Gly Ser Ser Asp Thr Ile Asp Met Thr Val Asn Ala His Cys His Gly
                210                 215                 220

Arg Arg Thr Asp Tyr Met Met Ser Ser Thr Gly Asn Leu Thr Val Thr
225                 230                 235                 240

Ser Asn Val Val Leu Leu Thr Phe Asp Leu Ser Tyr Ile Thr Pro Ile
                245                 250                 255

Pro Ser Asp Leu Ala Arg Leu Val Ser Gln Cys Gly Ile Pro Ser Cys
                260                 265                 270

Val Val Pro Cys Gly Arg Ile Ile His Pro Arg Phe Cys Asp Ser Cys
                275                 280                 285

Val Pro Ser Val Trp Gly Val Leu Glu Leu Thr Cys Leu His Asn Tyr
                290                 295                 300

Phe Pro Asn Arg Arg
305

<210> SEQ ID NO 7
<211> LENGTH: 314
<212> TYPE: PRT
<213> ORGANISM: Avian orthoreovirus

<400> SEQUENCE: 7

Met Ala Gly Leu Asn Pro Leu Gln Arg Arg Glu Val Val Ser Leu Ile
1               5                   10                  15

Leu Ser Leu Thr Ser Asn Val Asn Thr Asn Pro Gly Asp Leu Thr Ser
                20                  25                  30

Val Tyr Glu Arg Leu Thr Gly Leu Glu Ala Ser Thr Glu Ser Leu His
                35                  40                  45

Gln Ser Val Ser Ser Met Ala Ala Thr Val Ser Asp Ile Ser Ala Asp
    50                  55                  60

Leu Gln Gly Thr Thr Arg Ala Leu Asp Asp Val Thr Thr Leu Lys
65                  70                  75                  80

Ser Leu Ser Thr Ser Ile Thr Thr Leu Gln Asn Ser Val Thr Leu
                85                  90                  95

Ser Ala Thr Val Ala Glu Leu Thr Asp Thr Ser Ser Ala His Ser Gly
                100                 105                 110
```

```
Thr Leu Ser Ser Leu Gln Thr Val Ser Gly Asn Ser Asn Ala Ile
            115                 120                 125

Ala Ser Leu Lys Ser Asp Val Ser Ala Asn Ser Leu Ser Ile Thr Asp
    130                 135                 140

Leu Gln Asn Arg Val Lys Ser Leu Glu Ser Gly Thr Ser His Gly Leu
145                 150                 155                 160

Ser Phe Ser Pro Pro Leu Asn Ile Ala Asn Gly Val Val Ser Leu Asp
                165                 170                 175

Met Asp Pro Tyr Phe Cys Ser Gln Arg Val Ser Leu Thr Ser Tyr Ser
            180                 185                 190

Ala Glu Ala Gln Leu Met Gln Phe Gln Trp Val Ala Arg Gly Thr Thr
        195                 200                 205

Gly Ser Ser Asp Thr Ile Asp Met Thr Val Asn Ala His Cys His Gly
    210                 215                 220

Arg Arg Thr Asp Tyr Met Met Ser Ser Thr Gly Gly Leu Thr Val Ala
225                 230                 235                 240

Ser Asn Ala Val Ser Leu Thr Phe Asp Leu Asp Tyr Ile Thr Asn Met
                245                 250                 255

Pro Pro Asp Leu Ser Arg Leu Ile Pro Ser Ala Gly Phe Gln Ala Ala
            260                 265                 270

Ser Phe Pro Val Asp Ile Ser Phe Thr Arg Asp Ser Ser Thr His Thr
        275                 280                 285

Tyr Gln Val Tyr Gly Val Tyr Ser Ser Ser Arg Val Phe Thr Ile Thr
    290                 295                 300

Phe Pro Thr Gly Gly Asn Gly Thr Thr Asn
305                 310

<210> SEQ ID NO 8
<211> LENGTH: 314
<212> TYPE: PRT
<213> ORGANISM: Avian orthoreovirus
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (130)..(130)
<223> OTHER INFORMATION: Xaa can be any naturally occurring amino acid
<220> FEATURE:
<221> NAME/KEY: misc_feature
<222> LOCATION: (286)..(286)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid

<400> SEQUENCE: 8

Met Ala Gly Leu Asn Pro Leu Gln Arg Arg Glu Val Val Gly Leu Ile
1               5                   10                  15

Leu Ser Leu Thr Ser Asn Val Thr Thr Asn Pro Gly Asp Leu Lys Ser
            20                  25                  30

Ile His Glu Arg Leu Thr Ser Leu Glu Ala Ser Thr Glu Ser Leu His
```

-continued

```
                    35                  40                  45
Gln Ser Val Ser Ser Met Ser Ala Thr Leu Ser Asp Xaa Ser Ala Asp
 50                  55                  60
Leu Xaa Asp Thr Thr Arg Ala Leu Asp Asp Val Thr Val Thr Met Asn
 65                  70                  75                  80
Ser Leu Ser Ala Thr Ile Ala Ala Leu Gln Asn Ser Leu Thr Thr Leu
                 85                  90                  95
Ser Ala Thr Val Asp Glu Leu Thr Asp Thr Ser Ser Ala His Ser Gly
            100                 105                 110
Met Leu Ser Ser Leu Gln Thr Thr Val Asn Gly Asn Ser Ser Ala Ile
        115                 120                 125
Ser Xaa Leu Arg Ser Asp Val Ser Ala Asn Gly Leu Asn Ile Thr Asp
    130                 135                 140
Leu Gln Asn Arg Val Lys Ser Leu Glu Ser Asp Thr Ser His Gly Leu
145                 150                 155                 160
Ser Phe Ser Pro Leu Ser Val Ala Asp Gly Val Val Ser Leu Ser
                165                 170                 175
Met Asp Pro Tyr Phe Cys Ser Gln Arg Val Ser Leu Thr Ser Tyr Ser
            180                 185                 190
Ala Glu Ala Gln Leu Met Gln Phe Gln Trp Val Ala Lys Gly Thr Ser
        195                 200                 205
Gly Ser Ser Asp Thr Ile Asp Met Thr Val Asn Ala His Cys His Gly
    210                 215                 220
Arg Arg Thr Asp Tyr Met Met Ser Ser Thr Gly Leu Thr Val Thr
225                 230                 235                 240
Ser Asn Ala Val Ser Leu Thr Phe Asp Leu Asn Tyr Ile Thr Asn Met
                245                 250                 255
Pro Ser Asp Leu Ser Arg Leu Ile Pro Ser Ala Gly Phe Gln Val Ala
            260                 265                 270
Ser Phe Pro Val Asp Val Ser Phe Thr Arg Glu Ser Ser Xaa His Thr
        275                 280                 285
Tyr Gln Val Tyr Gly Ala Tyr Ser Ser Ala Arg Val Phe Thr Ile Thr
    290                 295                 300
Phe Pro Thr Xaa Val Xaa His Ile Lys His
305                 310

<210> SEQ ID NO 9
<211> LENGTH: 314
<212> TYPE: PRT
<213> ORGANISM: Avian orthoreovirus

<400> SEQUENCE: 9

Met Ala Gly Leu Thr Pro Leu Gln Arg Arg Glu Val Val Gly Leu Ile
 1                5                  10                  15
Leu Ser Leu Thr Ser Ser Gly Asn Thr Asn Cys Gly Asp Leu Thr Pro
                 20                  25                  30
Ile Tyr Asp Arg Leu Ser Ser Leu Glu Ser Ala Val Ala Ser Leu Asn
            35                  40                  45
Gly Ser Val Asn Gly Leu Leu Gln Lys Val Pro Asp Leu Glu Thr Asp
 50                  55                  60
Leu Gln Asn Val Val Ser Ser Leu Asp Gln Thr Asn Ser Thr Leu Ala
 65                  70                  75                  80
Glu Leu Ser Lys Glu Leu Arg Gln Leu Ser Ser Val Asp Asn Val
                 85                  90                  95
```

Val Thr Ser Ile Ser Asp Ile Ser Thr Val Ser Gly His Gln Asp
            100                 105                 110

Ala Ile Thr Ala Ile Gln Ile Ser Val His Ala Asn Thr Thr Ala Ile
        115                 120                 125

Thr Asn Leu Lys Ser Ser Ala Ser Thr Ala Ser Leu Lys Ile Thr Asp
    130                 135                 140

Leu Glu Arg Arg Val Glu Ala Ile Glu Ser Gly Ser Asp Ser Asn Leu
145                 150                 155                 160

Arg Phe Val Ser Pro Leu Ser Leu Ser Gln Gly Val Val Ser Leu Val
                165                 170                 175

Met Asp Pro Tyr Phe Cys Ser Asp Asn Gln Ala Leu Thr Ser Tyr Ser
            180                 185                 190

Thr Asp Ala Gln Leu Met Gln Phe Gln Trp Leu Ala Arg Gly Asp Asp
        195                 200                 205

Gly Ser Ser Ser Val Asp Met Leu Val Asn Ala His Cys His Gly
210                 215                 220

Arg Arg Thr Asp Tyr Met Met Ser Thr Thr Glu Ser Phe Thr Val Thr
225                 230                 235                 240

Gly Asn Ser Val Ser Leu Val Phe Asn Leu Asp Tyr Ile Thr Lys Pro
                245                 250                 255

Pro Thr Glu Met Ser Arg Leu Ile Pro Arg Ala Gly Phe Arg Ala Ala
            260                 265                 270

Ser Phe Pro Val Asp Val Ser Phe Thr Arg Asp Thr Thr His Ala
                275                 280                 285

Tyr Gln Val Tyr Gly Ala Phe Ser Ser Ala Arg Val Phe Lys Ile Thr
        290                 295                 300

Phe Leu Thr Gly Ala Leu Gly Arg Gln Phe
305                 310

<210> SEQ ID NO 10
<211> LENGTH: 312
<212> TYPE: PRT
<213> ORGANISM: Avian orthoreovirus

<400> SEQUENCE: 10

Met Ala Gly Leu Thr Pro Leu Gln Arg Arg Glu Val Val Gly Leu Ile
1               5                   10                  15

Leu Ser Leu Thr Ser Ser Gly Asn Thr Asn Cys Gly Asp Leu Thr Pro
            20                  25                  30

Ile Tyr Asp Arg Leu Ser Ser Leu Glu Ser Ala Val Ala Ser Leu Asn
        35                  40                  45

Gly Ser Val Asn Gly Leu Leu Gln Lys Val Pro Asp Leu Glu Thr Asp
    50                  55                  60

Leu Gln Asn Val Val Ser Leu Asp Gln Thr Asn Ser Thr Leu Ala
65                  70                  75                  80

Glu Leu Ser Lys Glu Leu Arg Gln Leu Ser Ser Val Asp Asn Val
                85                  90                  95

Val Thr Ser Ile Ser Gly Ile Ser Thr Thr Val Ser Gly His Gln Asp
            100                 105                 110

Ala Ile Thr Ala Ile Gln Ile Ser Val His Ala Asn Thr Thr Ala Ile
        115                 120                 125

Thr Asn Leu Lys Ser Ser Ala Ser Thr Ala Ser Leu Lys Ile Thr Asp
    130                 135                 140

Leu Glu Arg Arg Leu Glu Ala Val Glu Ser Gly Ser Asp Ser Asn Leu
145                 150                 155                 160

```
Arg Phe Val Ser Pro Leu Ser Leu Ser Gln Gly Val Ser Leu Val
            165                 170                 175

Met Asp Pro Tyr Phe Cys Ser Asp Asn Gln Ala Leu Thr Ser Tyr Ser
            180                 185                 190

Thr Asp Ala Gln Leu Met Gln Phe Gln Trp Leu Ala Arg Gly Asp Asp
            195                 200                 205

Gly Ser Ser Ser Val Asp Met Leu Val Asn Ala His Cys His Gly
    210                 215                 220

Arg Arg Thr Asp Tyr Met Met Ser Thr Thr Glu Ser Phe Thr Val Thr
225                 230                 235                 240

Gly Asn Ser Val Ser Leu Val Phe Asn Leu Asp Tyr Ile Thr Lys Pro
            245                 250                 255

Pro Thr Asp Met Ser Arg Leu Ile Pro Arg Ala Gly Phe Arg Ala Ala
            260                 265                 270

Ser Phe Pro Val Asp Val Ser Phe Thr Arg Asp Thr Thr His Ala
    275                 280                 285

Tyr Gln Val Tyr Gly Ala Phe Ser Ser Ala Arg Val Phe Lys Ile Thr
    290                 295                 300

Phe Leu Thr Gly Gly Thr Gly Thr
305                 310

<210> SEQ ID NO 11
<211> LENGTH: 315
<212> TYPE: PRT
<213> ORGANISM: Avian orthoreovirus

<400> SEQUENCE: 11

Met Ala Gly Leu Thr Pro Leu Gln Arg Arg Glu Val Val Gly Leu Ile
1               5                   10                  15

Leu Ser Leu Thr Ser Asn Ala Thr Thr Asn Cys Gly Asp Leu Thr Ala
            20                  25                  30

Ile Tyr Asn Arg Leu Leu Lys Leu Asp Ser Ser Val Glu Ser Leu Thr
            35                  40                  45

Thr Ser Val Gly Glu Leu Ser Lys Gln Phe Leu Ala Leu Glu Ser Gly
    50                  55                  60

Phe Gln Asn Val Glu Ser Ser Ile Gly Gln Leu Asn Thr Ser Phe Asp
65                  70                  75                  80

Thr Leu Ser Glu Glu Ala Arg Gln Leu Gln Ser Ser Val Thr Asp Ile
            85                  90                  95

Thr Asn Ser Ile Ser Ser Leu Ser Ala Thr Val Ser Glu His Gln Asn
            100                 105                 110

Ser Leu Ala Ala Leu Gln Thr Ser Val Gln Thr Asn Ile Thr Asp Ile
            115                 120                 125

Ala Asn Leu Lys Ser Ser Val Thr Thr Leu Ser Leu Thr Ala Thr Asp
    130                 135                 140

Leu Glu Arg Arg Leu Lys Val Ile Glu Ser Gly Ser Ser Ser Ser Leu
145                 150                 155                 160

Thr Phe Ser Ser Pro Leu Ser Leu Ser Asn Gly Val Val Ser Leu Asn
            165                 170                 175

Met Asp Pro Tyr Phe Cys Ser Asp Asn Tyr Ala Leu Thr Ser Tyr Ser
            180                 185                 190

Ser Asp Ala Gln Leu Met Gln Phe Gln Trp Leu Ala Arg Gly Asp
            195                 200                 205

Gly Ser Ser Gly Ser Val Glu Met Leu Val Asn Ala His Cys His Gly
```

```
                 210                 215                 220
Arg Arg Thr Asp Tyr Met Met Ser Thr Thr Glu Asn Leu Thr Val Thr
225                 230                 235                 240

Gly Asn Ser Thr Ser Leu Val Phe Ser Leu Glu Tyr Ile Thr Lys Pro
                245                 250                 255

Pro Ser Asp Met Ser Arg Leu Ile Pro Arg Ala Gly Phe Gln Ala Ala
                260                 265                 270

Ser Phe Pro Val Asp Val Ser Phe Thr Arg Asp Thr Ala Thr His Ala
                275                 280                 285

Tyr Gln Val Tyr Gly Val Phe Thr Thr Pro Arg Ile Phe Lys Ile Thr
                290                 295                 300

Phe Leu Thr Gly Gly Thr Gly Ala Ala Lys Phe
305                 310                 315

<210> SEQ ID NO 12
<211> LENGTH: 306
<212> TYPE: PRT
<213> ORGANISM: Avian orthoreovirus
<220> FEATURE:
<221> NAME/KEY: misc_feature
<222> LOCATION: (303)..(303)
<223> OTHER INFORMATION: Xaa can be any naturally occurring amino acid

<400> SEQUENCE: 12

Met Glu Gly Leu Thr Pro Leu Gln Arg Arg Glu Val Val Gly Leu Ile
1               5                   10                  15

Leu Ser Leu Thr Ser Ser Val Ser Ile Ser Pro Gly Asp Leu Ile Pro
                20                  25                  30

Leu Tyr Glu Arg Leu Ser Ala Val Glu Glu Thr Cys Ala Thr Val Asn
                35                  40                  45

Asp Ser Leu Gly Arg Leu Thr Ser Leu Val Ser Glu Ile Ser Ala Arg
50                  55                  60

Ile Asp Asp Leu Ala Arg Thr Leu Gln Asp Thr Ala Ala Gly Leu Asp
65                  70                  75                  80

Gly Val Gln Gly His Val Thr Thr Leu Gln Ser Ser Phe Asp Asp Leu
                85                  90                  95

Phe Ser Arg Val Ala Thr Leu Ser Ser Ser Val Ser Asn Gln Glu Ser
                100                 105                 110

His Leu Thr Thr Ile Ser Ala Ser Val Ser Thr Leu Ser Thr His Val
                115                 120                 125

Ser Asn Leu Gln His Asp Val Ser Ser Thr Ala Leu Thr Val Thr Ser
130                 135                 140

Leu Glu His Arg Val Glu Ala Leu Glu Ser Gly Ala Gly Ser Asp Leu
145                 150                 155                 160

Thr Phe Met Ala Pro Leu Lys Val Asp Gly Lys Ser Val Ser Leu Asp
                165                 170                 175

Leu Asp Pro Tyr Phe Cys Ser Glu Arg Thr Asn Leu Thr Ser Tyr Ser
                180                 185                 190

Ala Asn Ala Gln Leu Leu Gln Phe Gln Trp Leu Val Arg Ser Glu Gly
                195                 200                 205

Gly Ser Ser Asp Ser Ile Asp Met Asn Val Val Ala His Cys His Gly
210                 215                 220

Arg Arg Thr Asp Tyr Leu Met Ser Thr His Asp Ser Leu Thr Val Val
225                 230                 235                 240

Gly Asn Ser Val Thr Leu Ile Phe Asn Leu Asp Phe Ile Thr Thr Gln
                245                 250                 255
```

```
Gly Val Asp Tyr Ala Arg Leu Val Pro Cys His Gly Phe Gln Gln Ala
            260                 265                 270

Thr Phe Pro Val Asp Ile Ser Phe Thr Lys Gly Thr Ala Thr Gln Ser
            275                 280                 285

Tyr Gln Val Tyr Gly Ala Phe Asp Gly Pro Arg Ile Phe Lys Xaa Thr
            290                 295                 300

Phe Ser
305

<210> SEQ ID NO 13
<211> LENGTH: 313
<212> TYPE: PRT
<213> ORGANISM: Avian orthoreovirus

<400> SEQUENCE: 13

Met Ala Gly Leu Thr Pro Ser Gln Arg Arg Glu Val Val Gly Leu Ile
 1               5                  10                  15

Leu Ser Leu Thr Ser Asn Thr Ser Ile Asn Pro Gly Asp Leu Ala Pro
            20                  25                  30

Ile Tyr Ser Arg Leu Thr Ala Leu Glu Val Ala Arg Asp Glu Leu Asn
            35                  40                  45

Glu Ser Leu Ser Glu Leu Ser Ser Ala Val Ser Ala Leu Ser Thr Arg
 50                  55                  60

Phe Asp Asp Ala Ser Met Lys Leu Asn Ser Ile Thr Ala Asp Leu Thr
65                   70                  75                  80

Val Ile Lys Ser Asp Ile Ser Val Leu Asn Ser Ser Val Ser Gly Val
            85                  90                  95

Thr Ser Ser Met Ala Ala Leu Ser Gln Ser Val Ser Asn His Glu Ser
            100                 105                 110

Gln Leu Ala Thr Leu Ser Ser Ser Leu Ala Thr Leu Ser Ser Gln Val
            115                 120                 125

Ala Ala Leu Gln Arg Asp Val Ser Ala Ser Glu Leu Lys Leu Thr Asp
            130                 135                 140

Leu Gln His Arg Val Thr Ala Leu Glu Ser Ser Gly Gly Thr Ser Leu
145                 150                 155                 160

Arg Phe Leu Pro Pro Phe Lys Thr Asp Gly Ala Ser Val Ser Leu Glu
            165                 170                 175

Leu Asp Pro Tyr Phe Cys Ser Glu Arg His Asn Leu Thr Ser Tyr Ser
            180                 185                 190

Ala Ala Ala Gln Leu Leu Gln Phe Gln Trp Leu Val Lys Gly Glu Ser
            195                 200                 205

Gly Val Ser Asp Ser Phe Asp Met Asn Val Val Ala His Cys His Gly
            210                 215                 220

Arg Arg Thr Asp Tyr Leu Met Phe Thr Pro Ser Ser Leu Thr Val Thr
225                 230                 235                 240

Ser Asn Ser Val Ser Leu Val Phe Asp Leu Ser Phe Ile Ile Thr Pro
            245                 250                 255

Gln Ile Asp Leu Ala Arg Leu Val Pro Cys Tyr Gly Phe Gln Gln Ala
            260                 265                 270

Thr Phe Pro Val Asp Val Ser Tyr Thr Arg Gly Glu Asp Thr His Ser
            275                 280                 285

Tyr Gln Val Tyr Gly Ser Phe Asp Thr Pro Arg Ile Phe Lys Ile Thr
            290                 295                 300

Phe Ser Thr Gly Gly Thr Gly Thr Ala
```

<210> SEQ ID NO 14
<211> LENGTH: 276
<212> TYPE: PRT
<213> ORGANISM: Avian orthoreovirus

<400> SEQUENCE: 14

```
Met Asp Gly Leu Thr Gln Ser Gln Arg Arg Glu Val Val Gly Leu Ile
1               5                   10                  15
Leu Ser Leu Thr Ser Asn Val Thr Ile Asn Pro Gly Asp Leu Leu Gln
            20                  25                  30
Leu Arg Asn Arg Val Ser Ala Leu Glu Ser Ala Thr Ala Ser Leu Asn
        35                  40                  45
Glu Thr Val Lys Ala Thr Leu Asp Gln Leu Val Asp Leu Ser Gln Lys
    50                  55                  60
Leu Ser Asn Ala Ala Ala Ala Val Val Glu Ile Arg Arg Asp Leu Ser
65                  70                  75                  80
Ser Leu Thr Gly Asp Val Gln Val Val Gln Ser Ser Leu Glu Ser Leu
                85                  90                  95
Thr Asp Asp Met Ser Asp Leu Ser Asn Gln Val Asn Val Ser Ala Ser
            100                 105                 110
Ser Ile Thr Ser Leu Thr Ser Arg Val Asp Gly Leu Thr Val Asp Val
        115                 120                 125
Thr Asn Leu Lys Ser Asp Val Ser Lys Gln Gly Leu Lys Leu Asn Gly
    130                 135                 140
Leu Glu Gln Arg Val Ala Asn Leu Glu Asn Asp Thr Gly Ser Ala Tyr
145                 150                 155                 160
Thr Phe Ala Ala Pro Leu Lys Leu Asp Asn Gly Thr Val Ser Leu Asp
                165                 170                 175
Leu Asp Pro Tyr Phe Cys Ser Val Asp Arg Asn Leu Thr Ser Tyr Ser
            180                 185                 190
Ala Ser Ala Leu Leu Met Asn Phe Gln Trp Leu Val Arg Gly Glu Gly
        195                 200                 205
Gly Ser Ser Asp Ser Ile Asp Met Asn Val Thr Ala His Ser His Gly
    210                 215                 220
Gln Arg Thr Asp Tyr Met Met Ser Thr Thr Gln Ser Leu Thr Val Thr
225                 230                 235                 240
Gly Asn Ser Val Ser Leu Val Phe Asp Leu Asp Ala Leu Met Ser Pro
                245                 250                 255
Pro Thr Asp Tyr Ser Arg Leu Ile Pro Cys His Gly Phe Gln Gln Ala
            260                 265                 270
Thr Phe Pro Ser
        275
```

<210> SEQ ID NO 15
<211> LENGTH: 315
<212> TYPE: PRT
<213> ORGANISM: Avian orthoreovirus

<400> SEQUENCE: 15

```
Met Asp Gly Leu Thr Gln Ser Gln Arg Arg Glu Val Val Gly Leu Ile
1               5                   10                  15
Leu Ser Leu Thr Ser Asn Val Thr Ile Asn Pro Gly Asp Leu Leu Gln
            20                  25                  30
Leu Arg Asn Arg Val Ser Val Leu Glu Ser Ala Thr Ala Ser Leu Asn
```

```
                 35                  40                  45
Glu Thr Val Arg Ala Thr Leu Asp Gln Leu Val Asp Leu Ser Gln Lys
 50                  55                  60

Leu Ser Asn Ala Ala Ala Val Val Glu Ile Arg Arg Asp Leu Ser
 65                  70                  75                  80

Ser Leu Thr Gly Asp Val Gln Val Val Gln Ser Ser Leu Glu Ser Leu
                 85                  90                  95

Thr Asp Asp Thr Ser Asp Leu Ser Asn Gln Met Asn Val Ser Ala Ser
                100                 105                 110

Ser Ile Thr Ser Leu Thr Ser Arg Val Asp Gly Leu Thr Val Asp Val
                115                 120                 125

Thr Asn Leu Lys Ser Asp Val Ser Lys Gln Gly Leu Thr Leu Ser Gly
                130                 135                 140

Leu Glu Gln Arg Val Val Asn Leu Glu Asn Asp Thr Gly Ser Ala His
145                 150                 155                 160

Thr Phe Ala Ala Pro Leu Lys Leu Asp Asn Gly Thr Val Ser Leu Asp
                165                 170                 175

Leu Asp Pro Tyr Phe Cys Ser Val Asp His Asn Leu Thr Ser Tyr Ser
                180                 185                 190

Ala Ser Ala Leu Leu Met Asn Phe Gln Trp Leu Val Arg Gly Glu Gly
                195                 200                 205

Gly Ser Ser Asp Ser Ile Asp Met Asn Val Thr Ala His Ser His Gly
210                 215                 220

Gln Arg Thr Asp Tyr Met Met Ser Thr Thr Gln Ser Leu Thr Val Thr
225                 230                 235                 240

Gly Asn Ser Val Ser Leu Val Phe Asp Leu Asp Ala Leu Ile Ser Pro
                245                 250                 255

Pro Thr Asp Tyr Ser Arg Leu Ile Pro Cys His Gly Phe Gln Gln Ala
                260                 265                 270

Thr Phe Pro Val Asp Leu Ser Phe Lys Arg Asp Asp Ala Ala Tyr Ser
                275                 280                 285

Tyr Gln Val Tyr Gly Ser Phe Thr Ser Pro Arg Val Phe Lys Ile Thr
                290                 295                 300

Phe Ser Pro Gly Asn Ser Val Pro Ala Val Ile
305                 310                 315

<210> SEQ ID NO 16
<211> LENGTH: 318
<212> TYPE: PRT
<213> ORGANISM: Avian orthoreovirus

<400> SEQUENCE: 16

Met Asp Gly Leu Thr Gln Ser Gln Arg Arg Glu Val Val Arg Leu Ile
  1               5                  10                  15

Leu Ser Leu Thr Ser Asn Val Thr Ile Asn Pro Gly Asp Leu Thr Gln
                 20                  25                  30

Leu Arg Glu Arg Val Ser Ala Leu Glu Ser Ala Asn Ala Ser Leu Asn
                 35                  40                  45

Glu Thr Ile Arg Ala Val Leu Asp Gln Leu Val Asp Leu Ser Gln Gln
 50                  55                  60

Leu Gly His Ala Val Ala Ala Val Val Glu Met Arg Arg Asp Leu Asn
 65                  70                  75                  80

Ser Leu Thr Gly Asp Val Gln Thr Val Gln Ser Ser Leu Gly Pro Leu
                 85                  90                  95
```

-continued

```
Thr Asp Ser Val Ser Asp Leu Ser Ser Arg Val Thr Glu Ser Ser
                100                 105                 110

Ser Ile Thr Asn Leu Leu Gly Arg Val Asp Arg Leu Thr Asp Val
            115                 120                 125

Thr Asn Leu Lys Ser Asp Val Ser Asp Gln Gly Leu Lys Val Ser Ser
130                 135                 140

Leu Glu Gln Arg Val Thr Asn Leu Glu Thr Gly Thr Gly Ser Val Tyr
145                 150                 155                 160

Thr Phe Ala Ala Pro Leu Lys Leu Asp Gly Gly Thr Val Ser Leu Asp
                165                 170                 175

Leu Asp Pro Tyr Phe Cys Ser Val Asp His Asn Leu Thr Ser Tyr Ser
            180                 185                 190

Ala Ser Ala Gln Leu Met Asn Phe Gln Trp Leu Val Arg Gly Glu Gly
        195                 200                 205

Gly Ser Ser Asp Ser Ile Asp Met Asn Val Thr Ala His Ser His Gly
    210                 215                 220

Gln Arg Thr Asp Tyr Met Met Ser Thr Thr Gln Ser Leu Thr Val Thr
225                 230                 235                 240

Gly Asn Pro Val Ser Leu Val Phe Asp Leu Asn Ala Leu Thr Ser Pro
                245                 250                 255

Pro Ser Asp Tyr Ser Arg Leu Ile Pro Cys His Gly Phe Gln Gln Ala
            260                 265                 270

Thr Phe Pro Val Asp Leu Ser Phe Lys Arg Asp Asp Val Thr Tyr Ser
        275                 280                 285

Tyr Gln Val Tyr Gly Ser Tyr Thr Ser Pro Arg Val Phe Lys Ile Thr
    290                 295                 300

Phe Ser Pro Gly Asn Pro Val Pro Ala Ile Ile Arg Phe Ile
305                 310                 315

<210> SEQ ID NO 17
<211> LENGTH: 314
<212> TYPE: PRT
<213> ORGANISM: Avian orthoreovirus

<400> SEQUENCE: 17

Met Asp Gly Leu Thr Gln Gln Gln Arg Arg Glu Val Val Gly Leu Ile
1               5                   10                  15

Leu Ser Leu Thr Ser Ser Val Thr Ile Asn Pro Gly Asp Leu Thr Gln
            20                  25                  30

Ile Arg Glu Arg Leu Ser Ala Leu Glu Ser Ser Asn Ala Ser Leu Ser
        35                  40                  45

Glu Ser Val Gly Ala Val Ser Ser Lys Leu Ala Asp Leu Ser Val Val
    50                  55                  60

Leu Asp Asn Met Ala Val Ser Val Ala Glu Thr Arg Leu Glu Leu Ser
65                  70                  75                  80

Ser Val Ile Ser Asp Val Gln Ser Leu Arg Ser Ser Leu Asp Ser Ser
                85                  90                  95

Ile Ser Glu Leu Ala Ser Ile Ser Ser Leu Val His Asp His Ser Ser
            100                 105                 110

Ser Ile Ser Gly Leu Gln Arg Asp Asn Gly Ala Leu Ser Asn Glu Val
        115                 120                 125

Gly Asn Leu Lys Ser Ser Val Ser Ser Gln Gly Leu Thr Val Ser Ser
    130                 135                 140

Leu Glu Arg Arg Val Gln Ser Leu Glu Gly Ser Ser Ser Met Asn Leu
145                 150                 155                 160
```

```
Ser Phe Ala Asp Pro Leu Lys Leu Glu Asn Gly Thr Val Ser Leu Glu
            165                 170                 175

Leu Asp Pro Tyr Phe Cys Ser Val Ser Arg Asn Leu Thr Ser Tyr Ser
        180                 185                 190

Ala Asp Ala Gln Leu Met Gln Phe Gln Trp Ser Val Lys Gly Glu Asp
            195                 200                 205

Gly Ala Gly Asn Ser Ile Asp Met Asp Val Asn Ala His Cys His Gly
        210                 215                 220

Ser Arg Thr Asp Tyr Leu Met Ser Thr Lys Gln Ser Leu Thr Val Thr
225                 230                 235                 240

Thr Ser Pro Ala Thr Leu Val Phe Glu Leu Asp Arg Ile Val Ser Leu
            245                 250                 255

Pro Ser Asp Leu Ser Arg Leu Val Pro Cys Tyr Gly Phe Gln Gln Ala
            260                 265                 270

Thr Phe Pro Val Asp Ile Ser Phe Gln Arg Asp Gly Val Ser His Thr
        275                 280                 285

Tyr Gln Val Tyr Gly Thr Tyr Thr Ser Ser Arg Val Phe Lys Ile Thr
        290                 295                 300

Phe Ser Pro Gly Thr Pro Gly Pro Thr Gly
305                 310
```

<210> SEQ ID NO 18
<211> LENGTH: 315
<212> TYPE: PRT
<213> ORGANISM: Avian orthoreovirus
<220> FEATURE:
<221> NAME/KEY: misc_feature
<222> LOCATION: (314)..(314)
<223> OTHER INFORMATION: Xaa can be any naturally occurring amino acid

<400> SEQUENCE: 18

```
Met Asp Gly Leu Thr Gln Gln Arg Arg Glu Val Val Gly Leu Ile
1               5                   10                  15

Leu Ser Leu Thr Ser Ser Val Thr Ile Asn Pro Gly Asp Leu Ile Gln
            20                  25                  30

Ile Arg Glu Arg Leu Ser Ala Leu Glu Ser Ala Asn Val Ser Leu Asn
        35                  40                  45

Glu Ser Val Asp Met Val Leu Ser Lys Leu Ser Asp Leu Ser Val Ala
50                  55                  60

Leu Asp Asn Met Ala Val Ser Val Ala Glu Met Arg Val Gly Leu Ser
65                  70                  75                  80

Ser Leu Thr Ser Asp Val Gln Gly Leu Arg Ala Ser Leu Asp Ser Ser
            85                  90                  95

Ala Ser Glu Leu Thr Ser Leu Ser Leu Ser Val Gln Gly His Ser Ser
            100                 105                 110

Leu Ile Ser Asp Leu Gln Arg Glu Gly Arg Ala Leu Ser Val Glu Val
        115                 120                 125

Asp Asn Leu Lys Ser Ser Val Ser Ser His Gly Leu Thr Ile Ser Ser
130                 135                 140

Leu Glu Gln Arg Val Gln Ala Leu Glu Val Gly Ser Ser Ala Ser Leu
145                 150                 155                 160

Ser Phe Thr Asp Pro Leu Lys Leu Glu Ala Gly Thr Val Ser Leu Asp
            165                 170                 175

Leu Asp Pro Tyr Phe Cys Ser Val Asn Arg Asn Leu Thr Ser Tyr Ser
        180                 185                 190
```

-continued

```
Ala Ser Ala Gln Leu Met Ser Phe Gln Trp Ser Val Lys Gly Glu Asp
        195                 200                 205

Gly Ala Ser Asn Ser Ile Asp Met Asp Val Asn Ala His Cys His Gly
        210                 215                 220

Ser Arg Thr Asp Tyr Leu Met Ser Thr Lys Gln Ser Leu Thr Val Leu
225                 230                 235                 240

Thr Ser Pro Ala Thr Leu Val Phe Glu Leu Asp Arg Ile Ile Asn Ile
                245                 250                 255

Pro Ser Asp Leu Ser Arg Leu Ile Pro Cys His Gly Phe Arg Gln Ala
                260                 265                 270

Thr Phe Pro Val Asp Ile Ser Phe Gln Arg Asp Gly Ala Ser His Thr
                275                 280                 285

Tyr Gln Val Tyr Gly Thr Phe Thr Ser Ser Arg Ala Phe Lys Ile Thr
            290                 295                 300

Phe Ser Pro Gly Ser Ser Gly Pro Ala Xaa Phe
305                 310                 315

<210> SEQ ID NO 19
<211> LENGTH: 20
<212> TYPE: DNA
<213> ORGANISM: Artificial Sequence
<220> FEATURE:
<223> OTHER INFORMATION: PCR primer

<400> SEQUENCE: 19
agtatttgtg agtacgattg                                                20

<210> SEQ ID NO 20
<211> LENGTH: 17
<212> TYPE: DNA
<213> ORGANISM: Artificial Sequence
<220> FEATURE:
<223> OTHER INFORMATION: PCR primer

<400> SEQUENCE: 20
ggcgccacac cttaggt                                                   17
```

BROAD-SPECTRUM VACCINE AGAINST AVIAN REOVIRUS

CROSS-REFERENCE TO RELATED APPLICATIONS

This application is a national stage entry under 35 U.S.C. § 371 of PCT/EP2015/072810 filed on Oct. 2, 2015, which claims priority to EP Application 14187650.8 filed on Oct. 3, 2014. The content of PCT/EP2015/072810 is hereby incorporated by reference in its entirety.

The present invention relates to the field of veterinary vaccines, in particular to vaccines for poultry for reducing infection by avian Reovirus. Also to methods for the preparation of such a vaccine, and to medical uses of such vaccines.

Avian Reoviruses are taxonomically classified in the species Avian Orthoreovirus that is within the genus Orthoreovirus, and in the Reoviridae family. The virus particle is without envelope but has a double-shelled protein capsid. This capsid contains the double stranded RNA genome that exists of 10 segments. The genomic segments can be grouped in three size classes: large (L), middle (M), and small (S); viral proteins encoded from these segments are indicated by reference to these segments, respectively as: lambda (λ), mu (μ), or sigma (σ). An overview of the structure of an avian Reovirus is given in Benavente & Martinez-Costas (Virus Res., 2007, p. 105-119).

Avian Reoviruses are important pathogens causing severe disease in birds, and significant economic damage to commercial poultry farming operations; mostly chickens, but also turkeys and other types of birds may be affected. Serious disease and even mortality occurs mainly in young birds, because an age-related resistance to avian Reovirus symptoms and infection develops in birds from about 4 weeks old. Symptoms include among others enteric- and respiratory disease, myocarditis and hepatitis. Most typical is viral arthritis, leading to tenosynovitis (or: Reoviral arthritis) in joints and tendons. The resulting lameness causes difficulties in walking to feed bins. Alternatively, viral enteric disease leading to malabsorbtion prevents an effective conversion of the feed. Both diseases are especially troublesome for fast growing and heavier type breeds such as broilers (meat type birds). Also, in combination with several other viral and bacterial enteric disease agents, avian Reovirus is a factor in the so-called 'runting stunting syndrome'.

All these symptoms lead to animal suffering and to economic losses over reduced slaughter weights and condemnations for poor carcass qualities.

The main way to control avian Reovirus infection is by vaccination, either of the chicks directly at very young age, or by vaccination of breeders (mother hens that produce fertilised eggs for offspring) before their laying period, to reduce egg-transmission, and to protect the chicks indirectly via maternally derived antibodies.

Avian Reovirus can be cultivated in vitro, and replicates well for example on primary chicken-embryo liver cells. Replication causes a typical cytopathic effect (cpe) showing large cell-syncytia.

Avian Reovirus vaccines are usually whole virus vaccines, that are of the attenuated live-, or of the inactivated type. Examples of commercial avian Reovirus vaccines (all from MSD AH, the Netherlands) are: live vaccines: Nobilis® Reo 1133, or Nobilis® Reo 2177; or an inactivated-adjuvanted vaccine such as Nobilis® Reo Inac (comprising strains 1733 and 2408). The origins of the S1133 vaccine strain date back to the early 1980's (Van der Heide et al., 1983, Avian Dis., vol. 27, p. 698-706) but it is still in use today.

In the standard recommended vaccination regime, breeder birds are vaccinated against avian Reovirus at least two times: by a primary vaccination (priming) with live vaccine at very young age, and by a secondary vaccination (booster) with inactivated vaccine several weeks later. Depending on the severity of field infection pressure another booster may be given a few weeks later, and breeder birds typically receive a further booster vaccination at about 16-18 weeks old, i.e. 4-6 weeks before the onset of lay. In practice the infection-pressure by avian Reovirus in the field is not always high, therefore many poultry farmers suffice by giving only one vaccination to chicks or to breeders. However in the case of an outbreak of virulent avian Reovirus infection, the offspring chicks may not be sufficiently protected against a field infection.

Immune protection against avian Reovirus is obtained through an effective humoral immune response, against several of the virus' structural proteins. The main viral immunogens however are the outer capsid proteins sigmaB and sigmaC; sigmaB (or: σB) is the major, and sigmaC (σC) protein is the minor outer capsid protein. SigmaC serves in attachment of the viral particle to a host cell. It is encoded by the 3' region of the S1 genome-segment, and is about 326 amino acids in size. The sigmaC protein was found to be much more variable antigenically than sigmaB (WO 2009/093251, and: Meanger et al., 1995, Avian Pathol., vol. 24, p. 121-134).

The general belief in the field of avian Reovirus vaccinology was that an effective vaccination against avian Reovirus could only be obtained by a homologous vaccine, so against viruses from within the same serotype group as the vaccine antigen (Wood et al., 1986, Comp. Pathol., vol. 86, p. 125-129). For many years avian Reovirus vaccines have therefore been based on antigens from distinct single serotype groups. Standard vaccination programs were directed to the Reovirus serotype present in a local flock; repeated vaccination then provided solid immunity.

When more than one serotype of avian Reovirus was prevalent in an area, these vaccines could be alternated in priming and booster vaccination, for example by administering a priming vaccination with a 'classical' vaccine strain of avian Reovirus, such as S1133, 1733, 2177, or 2408, and following-up with a booster vaccine against e.g. an ERS strain. For many years these were the main types of avian Reovirus prevalent in the field.

As an RNA virus, avian Reovirus may develop mutations in its genome. In practice this leads to the occasional encounter of new variants in the field, which may be more or less virulent. A problem in that respect however is the difficulty of an effective differentiation of avian Reoviruses, as serological tests may show variability in results. Therefore avian Reovirus strains used to be identified by testing virus neutralisation using polyclonal sera in a plaque-reduction assay, or by determining a specific binding-pattern using a panel of monoclonal antibodies, see the characterisation of the 2177 strain (EP 687.728), and the ERS strain (EP 1.024.189).

Alternatively, avian Reovirus strains can be characterised by the main disease symptoms the virus induces, such as: tenosynovitis, malabsorbtion, or neurological symptoms (e.g. an ERS strain inducing neurological symptoms as is described in EP 1.551.961). However because of the heterogeneity in pathogenicity, this is not fully conclusive.

More recently, the classification of avian Reoviruses is done on the basis of molecular diagnostics, by comparing viral amino acid- or nucleotide sequences. Particularly useful in that respect was found to be the comparison of the amino acid sequence of the sigmaC protein, as that is the most variable of the avian Reovirus proteins: showing only 35% amino acid sequence identity between the least related avian isolates (J. M. Day, 2009, Inf. Gen. & Evolution, vol. 9, p. 390-400).

Several scientists have described the grouping of avian Reovirus isolates by phylogenetic analyses based on the amino acid sequence identity of their sigmaC proteins. As more and more sigmaC protein sequences from avian Reovirus isolates became available in public databases, more elaborate analyses became possible. For example: Kant et al. (2003, Vet. Res., vol. 34, p. 203-212), have described a division of avian Reoviruses into 5 main genotype groups. No correlation could be found between serotype- and genotype groups, or between disease- and genotype groups: all types of avian Reovirus-associated disease could result from infection with an avian Reovirus from any of the genotype groups.

Using different parameters, other phylogenetic studies based on sigmaC protein analyses describe another grouping: Liu et al. (2003, Virology, vol. 314, p. 336-349), define 6 lineages; and Lublin et al. (2011, vaccine, vol. 29, p. 8683-8688), define 4 genotype groups.

The system described by Kant et al. (into 5 genotype groups), seems to receive most scientific support. In that classification, the 'classical' avian Reovirus vaccine strains, all fall within Kant's genotype group 1, while the ERS strain falls into Kant's genotype group 5.

Lublin et al. (supra) studied vaccination against the different genotype groups. In line with the consensus that avian Reovirus vaccines mainly protect homologously, they found that a vaccine effective against all the different genotypes of avian Reovirus had to contain antigenic material from each of these genotype groups.

In recent years there has been a spike in the number of break-through infections of avian Reovirus. From about 2009-2013 several outbreaks of avian Reovirus occurred in Europe and the USA, whereby flocks of chickens showed symptoms of severe avian Reovirus infection with tenosynovitis, malabsorbtion and even mortality; this in spite of the fact that the chickens had been properly vaccinated with commercial avian Reovirus vaccines. This demonstrated that virulent new avian Reovirus strains had developed, and that the classical- and ERS type vaccines could not always protect effectively.

A number of outbreaks in 2011-2012 in two regions of France were analysed by Troxler et al. (2013, Vet. Record, vol. 172, p. 556). Relying on the division described by Kant et al. (supra) of avian Reovirus strains by amino acid sequence comparison of the SigmaC protein into 5 genotype groups, Troxler et al. classified the outbreak strains they isolated from France, as a subclass of Kant's genotype group 1.

Because current vaccines appeared ineffective against these modern break-through strains, Troxler et al. repeat the recommendation by Lublin et al. that a broad cross-protective vaccine would need to incorporate all the genotype groups of avian Reovirus.

Consequently, there exists a pressing need in the field of poultry farming, to have available a vaccine against avian Reovirus that is broadly protective, and is effective also against recent virulent break-through strains.

It is therefore an object of the present invention to overcome disadvantages in the prior art, and to accommodate to this need in the field by providing a vaccine that can reduce infection by a broad spectrum of avian Reoviruses, amongst others by recent virulent break-through strains of avian Reovirus.

Surprisingly it was found that this object can be met, and consequently disadvantages of the prior art can be overcome, by providing a vaccine for reducing infection by avian Reovirus, whereby the vaccine comprises avian Reovirus antigenic material that is derived from only two of the five genotype groups of avian Reovirus, based on amino acid sequence comparisons of the viral sigmaC protein.

Such a vaccine was found to provide broad-spectrum protection, by almost completely reducing the replication of recent breakthrough isolates of avian Reovirus, after only a single vaccination.

The inventors have analysed some 150 samples from outbreaks of avian Reovirus from between 1993 and 2013 and from several countries. Interestingly, when comparing the amino acid sequences of their sigmaC protein, the newly isolated avian Reoviruses belonged to all genotype groups as detailed below. This expands on the findings by Troxler et al., and shows that the recent outbreaks of avian Reovirus are not caused by any specific genotype of avian Reovirus. Rather there seems to be a general change of the virus' characteristics that makes the existing vaccines less effective. Consequently, there is a need for an update of the avian Reovirus vaccines, and the updated vaccine will need to protect against all existing genotypes of the virus.

For the present invention avian Reovirus strains and isolates are divided into 5 genotype groups, as defined herein, based on the amino acid sequence of their SigmaC protein. This gave an effective division of all known strains, as well as a way to classify recent breakthrough strains. Also, this division into 5 genotype groups was found to match closely with the genotype division as described by Kant et al. (supra).

The inventors were surprised to find that a vaccine based on a specific combination of antigenic material from two genotype groups of avian Reovirus: genotype groups 1 and 4, had a broad-spectrum protective effect. In contrast, a similar vaccine containing avian Reovirus antigenic material from genotype groups 1 and 5, did not provide such a broad protection.

This novel vaccine provided target avians with a broad-spectrum protection against the replication of avian Reovirus, as this vaccine could almost completely reduce the replication in a target by avian Reoviruses. This applied both to avian Reovirus from the same genotype group as the antigenic material comprised in the vaccine (homologous avian Reovirus), and to avian Reovirus from a genotype group that was different from that of which antigenic material was comprised in the vaccine (i.e. heterologous avian Reovirus). This vaccination effect was obtained already after a single vaccination, and was even effective against recent virulent outbreak strains of avian Reovirus.

As a result, this novel broad-spectrum vaccine against avian Reovirus reduces avian Reovirus induced disease in vaccinated animals. Also, by reduction of the viral load this reduces the spread of the virus.

This was unexpected, and in direct contrast to the general conviction in the field at the time of the invention, where the general belief was that avian Reovirus vaccines are only fully effective against homologous viruses, and could not provide effective heterologous protection over the different genotype groups, and that such vaccination by standard would require at least two administrations to be effective. Indeed this was confirmed by Lublin et al. (supra) who tested a broad avian Reovirus vaccine based on antigenic material from representatives of each of the described genotype groups.

Consequently, when following this recommendation in the field, the development of an effective vaccine with a broad range of protection against these modern breakthrough strains of avian Reovirus would require the inclusion of antigenic material of avian Reoviruses from all described genotype groups.

It is not known why this specific combination of antigenic material from avian Reovirus genotype groups 1 and 4 can provide such an effective broad-spectrum vaccination effect. Although the inventors do not want to be bound by any theory or model that might explain these observations, they speculate that this particular combination of antigenic material from avian Reovirus of genotype groups 1 and 4 must be presenting the immune system of a target avian with a combination of antigens that triggers an immune response that is cross-protective over a broad range of the antigen specificities that the different avian Reovirus genotype groups present.

Therefore in one aspect the invention provides a vaccine for reducing infection by avian Reovirus, the vaccine comprising avian Reovirus antigenic material that is derived from avian Reoviruses from more than a single genotype group and a pharmaceutically acceptable carrier, wherein the avian Reovirus antigenic material consists of antigenic material derived from avian Reoviruses from each one of two genotype groups: genotype group 1 and genotype group 4.

As is readily apparent to a person skilled in the art, such a broad-spectrum vaccine that can be based on only a limited number of antigens, provides several clear advantages over a more extensive combination vaccine comprising antigens from all genotype groups. These advantages lie mainly in the significant savings that can be obtained this way in labour and capital, due to the improved efficiency and simplicity of production, storage, and quality control.

A "vaccine" is well known to be a composition which has an inherent medical effect, comprising an immunologically active component, and a pharmaceutically acceptable carrier. The 'immunologically active component', is an antigenic (combination of) molecule(s) that is recognised by the immune system of the target which induces a protective immunological response. The response may originate from the target's innate and/or from the acquired immune system, and may be of the cellular and/or of the humoral type.

For the vaccine according to the invention, the immune response induced in the vaccinated target animal has the effect of "reducing infection by avian Reovirus". This refers to a reduction of the level or the extent of the infection, for example by reducing the viral load or shortening the duration of viral replication in the host animal.

This effect is obtained by preventing or reducing the establishment or the proliferation of a productive infection by avian Reovirus in its target organs such as tendon, or intestines. In turn this leads to a reduction in the target animal of the number, the intensity, or the severity of lesions and clinical signs that could be caused by the viral infection. Such a vaccine is colloquially referred to as a vaccine 'against' avian Reovirus, or as an 'avian Reovirus vaccine'.

The determination of the effectiveness of a vaccine according to the invention for reducing infection by avian Reovirus, is well within the skills of the routine practitioner, and can be done for instance by monitoring the immunological response following vaccination or after a challenge infection, e.g. by monitoring the targets' signs of disease, clinical scores, serological parameters, or by re-isolation of the pathogen, and comparing these results to a vaccination-challenge response seen in mock vaccinated animals.

Various embodiments, preferences and examples of a vaccine according to the invention will be outlined below.

An "avian Reovirus" is well known in the art, and is a virus belonging to the species avian Orthoreovirus. These viruses and their induced diseases are e.g. described in well-known handbooks, like: "The Merck veterinary manual" (10th ed., 2010, C. M. Kahn edt., ISBN: 091191093X), and: "Diseases of Poultry" (12th ed., 2008, Y. M. Saif edt., ISBN-10: 0813807182).

An avian Reovirus displays the characterising features of its taxonomic group-members such as the morphologic, genomic, and biochemical characteristics, as well as the biological characteristics such as physiologic, immunologic, or pathologic behaviour. As is known in the field, the classification of micro-organisms is based on a combination of such features. The invention therefore also includes avian Reoviruses that are sub-classified therefrom in any way, for instance as a subspecies, strain, isolate, genotype, variant, subtype or subgroup and the like.

It will be apparent to a skilled person that while an avian Reovirus for the present invention is currently classified in a particular species or genus, this is a taxonomic classification that could change in time as new insights lead to reclassification into a new or different taxonomic group. However, as this does not change the micro-organism itself, or its antigen repertoire, but only its scientific name or classification, such re-classified micro-organisms remain within the scope of the invention.

The term "comprising" (as well as variations such as "comprise", "comprises", and "comprised") as used herein, refer(s) to all elements, and in any possible combination conceivable for the invention, that are covered by or included in the text section, paragraph, claim, etc., in which this term is used, even if such elements or combinations are not explicitly recited; and does not refer to the exclusion of any of such element(s) or combinations. Consequently, any such text section, paragraph, claim, etc., can also relate to one or more embodiment(s) wherein the term "comprising" (or its variations) is replaced by terms such as "consist of", "consisting of", or "consist essentially of".

The "antigenic material" for the invention can in principle be any type of material derived from an avian Reovirus for the invention, provided it can induce a protective immune response (either by itself or with an adjuvant). The antigenic material must thus be of a size, structure, form, or quality such that the immune response it induces in the vaccinated target avian is of sufficient strength to be able to reduce infection by an avian Reovirus.

The antigenic material for the invention may be a replicative avian Reovirus (i.e. a 'life' avian Reovirus); an inactivated ('killed') avian Reovirus; or a part of an avian Reovirus such as a subunit, extract, fraction, homogenate or sonicate.

In case the antigenic material for the invention is a part of an avian Reovirus, it can be a protein, lipoprotein, glycoprotein, nucleic acid molecule, or a combination of one or more of these. The antigenic material may be of biologic or of synthetic origin, and may be derived directly or indirectly from an avian Reovirus for the invention.

For the invention, a "protein" refers to a molecular chain of amino acids. A protein is not of a specific length, structure or shape, and can if required, be modified in vivo or in vitro by e.g. glycosylation, amidation, carboxylation, phosphorylation, pegylation, or changes in spatial folding. A protein can be a native- or a mature protein, a pre- or pro-protein, or a part of a protein. A protein can be of biologic or synthetic origin. Inter alia, polypeptides and peptides, are included within this definition of protein.

For the invention, antigenic material is "derived from" an avian Reovirus for the invention if it is in any way obtained from an avian Reovirus or from a part thereof. The antigenic material obtained for the invention can conveniently be comprised in a carrier such as a buffer, and preferably will be in a liquid form, to allow the use or manipulation of the antigenic material for the invention. A skilled person is perfectly capable of selecting and using a suitable carrier for this purpose.

Examples of ways to derive antigenic material for the invention from an avian Reovirus may be to proliferate an avian Reovirus for the invention in an appropriate host cell, after which the virus can then be harvested, and isolated by standard techniques well known in the art. The harvested replicative virus can be used with or without the host cell or parts thereof.

Avian Reovirus for the invention can also be obtained in inactivated form, by treating replicative avian Reovirus with any suitable technique such as with heat, radiation, or with chemicals such as formalin, beta-propiolactone, binary ethyleneimine, or beta-ethanolamine.

Further, antigenic material derived from an avian Reovirus for the invention, may be a part of an avian Reovirus, such as a subunit, extract, fraction, homogenate, or sonicate. These can be prepared by standard techniques well known in the art, and can start from replicative-, or from inactivated virus. The virus used can be derived from a viral culture, such as from the cell-pellet, the culture supernatant, or the whole culture.

Antigenic material for the invention can also be derived by expression of an avian Reoviral gene in cells of a recombinant DNA expression system: these cells, the supernatant, or the whole culture can be harvested and purified e.g. by centrifugation or filtration, optionally followed by concentration. Alternatively, when the expressed protein remains within the cells of the expression system, these cells can be harvested, and the protein can be produced as a subunit, extract, fraction, homogenate or sonicate of these cells. All this is well-known in the art. Convenient expression systems are from bacterial, yeast, insect, plant, or mammalian origin; e.g.: *Escherichia coli, Bacillus subtilis, Lactobacillus* sp., or *Caulobacter crescentus; Sacharomyces cereviseae, Pichia pastoris*; Insect-cell/Baculovirus, *Drosophila*; Tobacco; or Hela or CHO cells.

The required methods and materials to obtain avian Reovirus antigenic material for the invention are standard techniques in virology, biochemistry and molecular biology, all well known to a skilled person. For example, molecular-biological techniques and materials to obtain viral RNA from an avian Reovirus for the invention, to prepare cDNA, and to manipulate this for expression, are well known in the art, and are e.g. described extensively in well-known handbooks such as: Current Protocols in Molecular Biology, John Wiley & Sons, N.Y. (1989); Basic Methods in Molecular Biology, Elsevier Science Publishing Co., Inc., N.Y. (1986); and: Sambrook & Russell, 2001, in: 'Molecular cloning: a laboratory manual', 3rd ed. New York, USA: Cold Spring Harbour Laboratory Press.

A "genotype group" in the context of an avian Reovirus for the invention, refers to a number of avian Reovirus isolates that can be grouped together based on the results of an alignment of the amino acid sequence of their Sigma C protein, as described herein. The members in such a group are related by sharing a certain minimal level of amino acid sequence identity for their sigmaC protein. This way 5 genotype groups of avian Reovirus were defined.

Such an amino acid sequence identity comparison is a well-known way to determine the evolutionary relatedness or 'phylogeny' between proteins. It is expressed as a percentage of amino acids that are identical when comparing corresponding positions between amino acid sequences, in relation to the length of the aligned protein in number of amino acids. NB: this is not to be confused with sequence similarity, where amino acids that are different but similar are also counted.

Such an alignment is preferably performed using a computer program to do automated (multiple) pairwise alignments.

For the purpose of establishing an avian Reovirus genotype group for the invention, the decisive test is by using the computer program: "BLAST 2 SEQUENCES", available at the NCBI website (by selecting "bl2seq", and sub-program: "blastP", that can be found at: http://blast.ncbi.nlm.nih.gov/Blast.cgi), using its default parameter settings. The program optimises the way two sequences are aligned, and displays the region of overlap, and the number and the percentage of identical matches between amino acids.

For the invention, the amino acid sequence alignment is made over amino acids 1-277 of the sigmaC protein, with the methionine deriving from the start codon counting as amino acid no. 1.

Lists of alignment scores of avian Reoviruses in the various genotype groups, are presented in the Tables attached hereto.

To represent the evolutionary relationships within, and among genotype groups, alignment results can be presented as a phylogenetic tree. This can also be done by computer, for instance using the program PHYLIP or MEGA (Tamura et al., 2013, Mol. Biol. and Evol., vol. 30, p. 2725-2729; most recent version: MEGA6). Figures representing such phylogenetic trees of the genotype groups of the avian Reoviruses analysed for the invention, are represented in the Figures attached hereto.

In public databases such as GenBank or EMBL over 200 amino acid sequences are currently available of sigmaC proteins from a wide variety of avian Reovirus isolates. This allowed making comparative alignments, and classification of public avian Reovirus strains into genotype groups as defined herein.

In addition to this large amount of public sequence information, the inventors had available the amino acid sequences of sigmaC proteins from many recent outbreak strains. Details are described in the Examples section below; in short: a tissue sample was homogenised, and cultured to amplify any virus. Viral RNA was extracted, and using SigmaC specific primers (Liu et al., supra) in an RT-PCR, the section of the avian Reovirus genome encoding the sigmaC protein was amplified, all using standard techniques. Next the nucleic acid sequence of this cDNA was determined, and the DNA sequence translated into a putative amino acid sequence. This was then compared to other sigmaC sequences, for determining the genotype group of the outbreak isolate. As described, representatives of all 5 genotype groups were identified among the outbreak isolates.

The sigmaC protein amino acid sequence from a number of representative breakthrough isolates from all 5 genotype groups, is presented in the attached sequence listing.

From these analyses it was found that an avian Reovirus for the invention is classified as belonging to genotype group 1 when that avian Reovirus, in a replicative form contains genetic information encoding a sigmaC protein having an amino acid sequence that has at least 57% amino acid sequence identity with the amino acid sequence of SEQ ID NO. 1 (amino acid sequence of the SigmaC protein of avian Reovirus isolate SL11A0823-2 BE).

Similarly, an avian Reovirus for the invention is classified as belonging to genotype group 4 when that avian Reovirus, in a replicative form contains genetic information encoding a sigmaC protein having an amino acid sequence that has at least 66% amino acid sequence identity with the amino acid sequence of SEQ ID NO. 4 (amino acid sequence of isolate nr. SL11A0823-1 BE).

The terms "in a replicative form" are used to refer to an avian Reovirus that is capable of replication, i.e. is replicative, non-inactivated, or 'live' virus. So, the vaccine according to the invention employs antigenic material that is derived from an avian Reovirus that at some point in time was in a replicative form, and then contained genetic information encoding a sigmaC protein with the identity level specified. However, this does not mean that the antigenic material itself still needs to contain that genetic information at all, or intact.

A "pharmaceutically acceptable carrier" is an aid in the preparation, storage, or administration of the immuno-active compound of a vaccine, without causing (severe) adverse effects to the health of the target animal to which it is administered. Such a carrier can for instance be sterile water, or physiological salt or phosphate buffered saline solutions. In a more complex form the carrier can e.g. be a buffer, which can comprise further additives, such as stabilisers or preservatives. Details and examples are for instance described in well-known handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

Avian Reoviruses that belong to genotype groups 1 or 4 can thus be employed for preparing a vaccine according to the invention. Such avian Reoviruses are described in detail herein in the Examples section, also they are well known in the art, and can readily be obtained by a skilled person.

For example, avian Reoviruses can be used from publicly available avian Reovirus samples; these may already be classified as belonging to genotype groups 1 or 4, or can easily be classified as described herein. Such samples are available from a variety of universities and (poultry-) research institutions, as well as from depository institutes such as the ATCC (Manassas, Va., USA), the CNCM (Institut Pasteur, Paris, France), or the ECACC (Porton Down, UK).

Alternatively, avian Reovirus of genotype groups 1 and 4 can be obtained from field samples of chickens displaying clinical signs of avian Reovirus infection such as viral arthritis or malabsorbtion. Samples can be obtained from organs of affected birds such as from: tendon, hock joint, liver, spleen, or intestine such as jejunum. Virus can be cultured in vitro and can be identified as an avian Reovirus for example from its typical cpe in cell-culture, or using avian Reovirus specific antibodies. Also viral RNA can be analysed by RT-PCR, using primers as described in literature or herein. Next computer analysis of the sigmaC amino acid sequence will indicate the genotype group of the sample.

Using these methods, the inventors have isolated and analysed a large number of avian Reovirus isolates. A vaccine according to the invention was prepared from two of these that were isolated from avian Reovirus break-throughs in different chicken farms in Belgium in 2011; the isolate names are: SL11A0823-2BE and SL11A0823-1BE. These were classified as belonging to genotype groups 1 and 4 as defined herein, respectively. The amino acid sequence of their sigmaC protein is presented in SEQ ID NO's: 1 and 4 respectively.

Vaccines were prepared using standard procedures, in short: virus had been amplified from the field sample, and was plaque purified three times. Next virus was cultured on Vero cells, was inactivated using formalin, and concentrated, then viral antigenic material was formulated as a water-in-oil emulsion with light mineral oil and emulsifiers.

A single dose of vaccine was administered once to SPF layer chickens in different treatment groups, by intramuscular administration. Fertilised eggs from these vaccinated chickens were collected starting from 5 weeks after the vaccination. These were hatched, and offspring chicks were given a challenge inoculation with replicative avian Reovirus from different genotype groups. Vaccine efficacy for the offspring was determined by detection of challenge virus in blood samples taken at 3 days after the challenge inoculation.

The vaccination results are described in detail in the Examples section, but an effective broad-spectrum protection was only observed for the vaccine containing avian Reovirus antigens from genotype groups 1 and 4: almost no challenge virus could be isolated from chicks receiving the various homologous or heterologous challenge inoculations.

In contrast, groups of chicks receiving a vaccine containing antigenic material from only a single isolate of avian Reovirus, was only protected against the homologous challenge strain; non-vaccinated controls were positive for challenge virus in all samples; and a combination vaccine with avian Reovirus antigens from genotype groups 1 and 5 only protected against challenge virus from genotype groups 1 or 2, the same as a multivalent genotype 1 vaccine.

In a preferred embodiment, an avian Reovirus belonging to genotype group 1 according to the invention, contains (in replicative form) genetic information encoding a sigmaC protein having an amino acid sequence that has at least 58% amino acid sequence identity with the amino acid sequence of SEQ ID NO. 1. More preferred: 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% amino acid sequence identity with the amino acid sequence of SEQ ID NO. 1, in that order of preference.

In a preferred embodiment, an avian Reovirus belonging to genotype group 4 according to the invention, contains (in replicative form) genetic information encoding a sigmaC protein having an amino acid sequence that has at least 67% amino acid sequence identity with the amino acid sequence of SEQ ID NO. 4. More preferred: 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% amino acid sequence identity with the amino acid sequence of SEQ ID NO. 4, in that order of preference.

In an embodiment of a vaccine according to the invention, the avian Reovirus antigenic material consists of antigenic material derived from two kinds of avian Reovirus; the first kind is an avian Reovirus that in a replicative form contains genetic information encoding a sigmaC protein having an amino acid sequence that has at least 57% amino acid sequence identity with the amino acid sequence of SEQ ID NO. 1; and the second kind is an avian Reovirus that in a replicative form contains genetic information encoding a sigmaC protein having an amino acid sequence that has at least 66% amino acid sequence identity with the amino acid sequence of SEQ ID NO. 4.

For the invention, the indications "first" and "second" are used only for ease of reference, and not to indicate any numerical order or dependency.

In a preferred embodiment, a first kind of avian Reovirus contains (in replicative form) genetic information encoding a sigmaC protein having an amino acid sequence that has at least 58% amino acid sequence identity with the amino acid sequence of SEQ ID NO. 1. More preferred: 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% amino acid sequence identity with the amino acid sequence of SEQ ID NO. 1, in that order of preference.

In a preferred embodiment, a second kind of avian Reovirus contains (in replicative form) genetic information encoding a sigmaC protein having an amino acid sequence that has at least 67% amino acid sequence identity with the amino acid sequence of SEQ ID NO. 4. More preferred: 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or even 100% amino acid sequence identity with the amino acid sequence of SEQ ID NO. 4, in that order of preference.

In their analyses of the recent break-through strains of avian Reovirus, the inventors found that most of the isolates that classified as genotype group 1 (as defined herein), in fact formed a genotype subgroup that was clearly distinct from the classical vaccine type strains that also belong in the genotype group 1. This is also in line with the findings of Troxler et al. (supra). The inventors therefore refer to the genotype group of the classical avian Reovirus vaccine strains as genotype subgroup 1A and to the genotype group of this section of break-through isolates as genotype subgroup 1B.

Therefore, in an embodiment of a vaccine according to the invention, the antigenic material derived from avian Reovirus from genotype group 1, is derived from avian Reovirus from genotype subgroup 1B.

An avian Reovirus for the invention is classified as belonging to genotype subgroup 1B when that avian Reovirus, in a replicative form contains genetic information encoding a sigmaC protein having an amino acid sequence that has at least 78% amino acid sequence identity with the amino acid sequence of SEQ ID NO. 1.

In a further embodiment, an avian Reovirus belonging to genotype subgroup 1B according to the invention, contains (in replicative form) genetic information encoding a sigmaC protein having an amino acid sequence that has at least 79% amino acid sequence identity with the amino acid sequence of SEQ ID NO. 1. More preferred: 80, 81, 82, 83, 84, 85, 86, 87, 88, 89, 90, 91, 92, 93, 94, 95, 96, 97, 98, 99 or even 100% amino acid sequence identity with the amino acid sequence of SEQ ID NO. 1, in that order of preference.

In order to properly characterise the other genotype groups of avian Reovirus that are employed herein, these can also be defined by way of the level of amino acid sequence identity of their SigmaC protein in relation to a reference amino acid sequence:

An avian Reovirus is classified for the invention as belonging to genotype subgroup 1A when that avian Reovirus, in a replicative form contains genetic information encoding a sigmaC protein having an amino acid sequence that has at least 79% amino acid sequence identity with the amino acid sequence represented in GenBank accession number AAB61607 (avian Reovirus strain 1733). More preferred: 80, 81, 82, 83, 84, 85, 86, 87, 88, 89, 90, 91, 92, 93, 94, 95, 96, 97, 98, 99 or even 100% amino acid sequence identity with the amino acid sequence represented in GenBank accession number AAB61607, in that order of preference.

An avian Reovirus is classified for the invention as belonging to genotype group 2 when that avian Reovirus, in a replicative form contains genetic information encoding a sigmaC protein having an amino acid sequence that has at least 58% amino acid sequence identity with the amino acid sequence of SEQ ID NO. 2 (amino acid sequence of the SigmaC protein of avian Reovirus isolate SL11A0294-12 FR). More preferred: 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% amino acid sequence identity with the amino acid sequence of SEQ ID NO. 2, in that order of preference.

An avian Reovirus is classified for the invention as belonging to genotype group 3 when that avian Reovirus, in a replicative form contains genetic information encoding a sigmaC protein having an amino acid sequence that has at least 57% amino acid sequence identity with the amino acid sequence of SEQ ID NO. 3 (amino acid sequence of the SigmaC protein of avian Reovirus isolate SL10A1581-32 ES). More preferred: 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% amino acid sequence identity with the amino acid sequence of SEQ ID NO. 3, in that order of preference.

An avian Reovirus is classified for the invention as belonging to genotype group 5 when that avian Reovirus, in a replicative form contains genetic information encoding a sigmaC protein having an amino acid sequence that has at least 65% amino acid sequence identity with the amino acid sequence of SEQ ID NO. 5 (amino acid sequence of the SigmaC protein of avian Reovirus strain ERS). More preferred: 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or even 100% amino acid sequence identity with the amino acid sequence of SEQ ID NO. 5, in that order of preference.

In an embodiment antigenic material for the invention that is derived from avian Reovirus is: replicative avian Reovirus, inactivated avian Reovirus, or a part of avian Reovirus, such as a subunit, extract, fraction, homogenate or sonicate of avian Reovirus. More preferred is inactivated avian Reovirus.

When the antigenic material is inactivated avian Reovirus, or is a part of avian Reovirus, the antigenic material still contains (all the) components of an avian Reovirus that contribute to an immune response.

The amount of avian Reovirus antigenic material comprised in a vaccine according to the invention, when that antigenic material is inactivated avian Reovirus, or is a part of avian Reovirus, is between about 1 and about 1000 µg per animal dose. Preferable the amount of avian Reovirus antigenic material is between about 10 and about 500 µg/dose; more preferably between 10 and 250 µg/dose, and between 25 and 100 µg/animal dose.

For the invention, the preferred amount of avian Reovirus antigenic material per animal dose can relate to the amount of the antigenic material from each of the two genotype groups 1 and 4 separately, or to the amount of both combined. Also, the amount of antigenic material per animal dose from one genotype group does not need to be the same as that of the antigenic material of the other genotype group.

This last embodiment allows for further optimisation of the efficacy of the vaccine according to the invention, by adapting the amount of antigen, in absolute and in relative sense.

When antigenic material derived from an avian Reovirus for the invention is in the form of inactivated avian Reovirus, or is a part of avian Reovirus, then the amount per animal dose can be expressed by reference to the amount of replicative virus that was used for the inactivation or the extraction, fractionation, homogenisation, etc. Alternatively the amount per animal dose can be expressed in biochemical terms, e.g. as an amount of protein, or in arbitrary Elisa units, relative to a known standard. All this is well known to the skilled artisan.

When antigenic material derived from an avian Reovirus for the invention is in the form of replicative avian Reovirus, then the amount of the virus per animal dose of a vaccine according to the invention, is not as critical as when the vaccine would be based on inactivated avian Reovirus or on a subunit thereof. This is because the replicative avian Reovirus will multiply in the target avian up to a level of vireamia that is biologically sustainable. Nevertheless, a minimal dose must be given to achieve an effective 'take' of the 'life' vaccine. In this respect different ways exist to quantify a replicative avian Reovirus; convenient is one that counts the actual viable virus particles, such as in a tissue culture titration experiment, or in a plaque assay on a susceptible cell-layer. Amounts of the avian Reovirus for the invention can then be expressed as a number of units in tissue culture infective dose 50% (TCID50), or plaque forming units (pfu). Also, what constitutes an effective inoculum dose depends on the viability and replicative strength of the particular Reovirus that is used for the invention.

When the antigenic material derived from an avian Reovirus for the invention is in the form of replicative avian Reovirus, a preferred amount of replicative avian Reovirus for the vaccine according to the invention is between about 10 and about $1\times10^7$ TCID50 of the avian Reovirus per animal dose, more preferably between $1\times10^2$ and $1\times10^6$, between $1\times10^2$ and $1\times10^5$, between $1\times10^2$ and $1\times10^4$, and even between 500 and 5000 TCID50/dose, in this order of preference.

Vaccines according to the invention, can be administered in a volume that is acceptable for the target animal, and can for instance be between about 0.1 and about 10 ml in volume. Preferably one dose is in a volume between about 0.2 and about 3 ml.

In an embodiment a vaccine according to the invention additionally comprises a stabiliser. This may serve to protect degradation-prone components, and/or to enhance the shelf-life of the vaccine. Generally such stabilisers are large molecules of high molecular weight, such as lipids, carbohydrates, or proteins; for instance milk-powder, gelatine, serum albumin, sorbitol, sucrose, trehalose, spermidine, NZ amines, Dextrane or polyvinyl pyrrolidone, and buffers, such as alkali metal phosphates.

Preferably the stabiliser is free of compounds of animal origin, or even: is chemically defined, as disclosed in WO 2006/094.974.

Also preservatives may be added, such as thimerosal, merthiolate, phenolic compounds, and/or gentamicin.

General techniques and procedures in vaccinology are well known in the art and are described for instance in governmental regulations such as the Pharmacopoeia, and in well-known handbooks such as: "Remington" and "Veterinary vaccinology" (supra).

Target animals for a vaccine according to the invention are avians that are susceptible to infection with avian Reovirus. Preferred avian targets are avian species of relevance to humans or to the veterinary field, for example: chicken, turkey, duck, goose, partridge, peacock, quail, pigeon, pheasant, guinea fowl, finch, crow, parakeet, parrot, ara, macaw, cockatoo, finch, falcon, hawk, emu, cassowary, or ostrich.

Preferred are avian target species selected from the group consisting of: chicken, turkey, duck and goose. More preferred is: chicken, because for this avian target species the economic impact of avian Reovirus infection and disease is most pronounced.

For the invention, an avian may be of any type, breed, or variety, such as: layers, breeders, broilers, combination breeds, or parental lines of any of such breeds. Preferred types are: broiler, breeder, and layer. Most preferred are breeder chickens, as for this type of birds their vaccination results in protection of their offspring, which is most susceptible for infection with avian Reovirus.

For the invention it is not necessary that the avian species that is the target for vaccination, is the same as the avian species from which the avian Reovirus was isolated that was used for deriving antigenic material for the vaccine according to the invention.

In a preferred embodiment an avian Reovirus that was isolated from a chicken is used for a vaccine according to the invention.

A vaccine according to the invention can serve as an effective priming vaccination, which can later be followed and amplified by a booster vaccination.

The target animal for the vaccine according to the invention can in principle be healthy or diseased, and may be positive or -negative for presence of avian Reovirus, or for antibodies against avian Reovirus. Also the target can be of any age at which it is susceptible to the vaccination. However it is evidently favourable to vaccinate healthy, uninfected targets, and to vaccinate as early as possible to prevent any field infection.

A vaccine according to the invention can thus be used either as a prophylactic- or as a therapeutic treatment, or both, as it interferes both with the establishment and with the progression of an infection by an avian Reovirus.

In that respect, a further advantageous effect of the reduction of viral load by the vaccine according to the invention, is the prevention or reduction of shedding and thereby the spread of the virus, both vertically to offspring, and horizontally within a flock or population, and within a geographical area. Consequently, the use of a vaccine according to the invention leads to a reduction of the prevalence of avian Reovirus.

Therefore further aspects of the invention are:
the use of a vaccine according to the invention for reducing the prevalence of avian Reovirus in a population or in a geographical area, and
the vaccine according to the invention for reducing the prevalence of avian Reovirus in a population or in a geographical area.

The scheme for the administration of a vaccine according to the invention to a target avian can be in single or multiple doses, which may be given simultaneous, concurrent or sequentially, in a manner compatible with the intended dosage and formulation, and in such an amount as will be immunologically effective.

The scheme for the administration of a vaccine according to the invention ideally is integrated into existing vaccination schedules of other vaccines that the target avian may require, to reduce stress to the avians and to reduce labour costs.

The avian Reovirus vaccine according to the invention in principle can be given to an avian target by different routes of application, and at different points in their lifetime, provided the administered vaccine can establish an effective immune response.

In an embodiment a vaccine according to the invention is administered to chicks at the day of hatch or shortly thereafter, i.e. on day 1-3 of age. Alternatively, the vaccine according to the invention is administered in ovo, shortly before hatch; for chickens this is at about day 18 of embryonic development.

The vaccine according to the invention is preferably administered to an avian target animal, not less than 4 weeks before the expected onset of lay.

In this way, offspring can be effectively protected by maternally derived antibodies, and/or infection by vertical transmission is reduced or prevented.

Preferred routes for the administration of a vaccine according to the invention to a target avian are: as a parenteral application by injection, e.g. intramuscular or subcutaneous; by coarse drops, e.g. as a spray, eyedrop or oro-nasal application; or via the alimentary route.

The preferred application route is by intramuscular or by subcutaneous injection; preferably intramuscularly in the thigh- or breast muscle, or subcutaneously in the neck. This applies equally for when the antigenic material of an avian Reovirus for the invention is replicative virus, inactivated virus, or a subunit.

It goes without saying that the optimal route of application will depend on the specific vaccine formulation that is used, and on the particular characteristics of the target avian.

It is well within reach of the skilled person to further optimise a vaccine according to the invention. Generally this involves the fine-tuning of the efficacy of the vaccine, so that it provides sufficient immune-protection. This can be done by adapting the vaccine dose, or by using the vaccine in another form or formulation, or by adapting the other constituents of the vaccine (e.g. the stabiliser or the adjuvant), or by application via a different route.

The vaccine may additionally comprise other compounds, such as an adjuvant, an additional antigen, a cytokine, etc. Alternatively, a vaccine according to the invention can advantageously be combined with a pharmaceutical component for example an antibiotic, a hormone, an anti-inflammatory- or an anti-parasitic drug.

In an embodiment, a vaccine according to the invention comprises an adjuvant.

This applies in particular when the antigenic material derived from an avian Reovirus for the invention is in the form of inactivated virus, or is a part of an avian Reovirus according to the invention. As non-replicative forms such antigenic materials typically require additional immune stimulation to be able to induce an effective broad-spectrum vaccination.

An "adjuvant" is a well-known vaccine ingredient, which in general is a substance that stimulates the immune response of the target in a non-specific manner. Many different adjuvants are known in the art. Examples of adjuvants are Freund's Complete and -Incomplete adjuvant, vitamin E, aluminium compositions such as Aluminium-phosphate or Aluminium-hydroxide, non-ionic block polymers and polyamines such as dextransulphate, Carbopol®, pyran, Saponin, such as: Quil A®, or Q-vac®. Saponin and vaccine components may be combined in an ISCOM® (EP 109.942, EP 180.564, EP 242.380).

Furthermore, peptides such as muramyldipeptides, dimethylglycine, tuftsin, are often used as adjuvant, and oil-emulsions, using mineral oil e.g. Bayol™ or Markol™, Montanide™ or light mineral (paraffin) oil; or non-mineral oil such as squalene, squalane, or vegetable oils, e.g. ethyl-oleate. Also combination products such as ISA™ from Seppic™, or DiluvacForte™ can advantageously be used. An emulsion can be water-in-oil (w/o), oil-in-water (o/w), water-in-oil-in-water (w/o/w), or a double oil-emulsion (DOE), etc.

In a preferred embodiment, a vaccine according to the invention comprises a water-in-oil emulsion.

Such emulsion provides a depot effect in the vaccinated animal that slowly releases the antigen, thereby providing a prolonged stimulation of the target's immune system.

In a preferred embodiment, the oily phase of the water-in-oil emulsion comprises a mineral oil, or an ethyl-oleate.

In an embodiment of the vaccine according to the invention, the antigenic material is inactivated avian Reovirus that is formulated in a water-in-oil emulsion, whereby the oily phase of the water-in-oil emulsion comprises a mineral oil, or an ethyl-oleate.

It goes without saying that other ways of adjuvating, adding vehicle compounds or diluents, emulsifying or stabilizing a vaccine according to the invention are also within the scope of the invention.

In an embodiment, a vaccine according to the invention additionally comprises an oligodeoxynucleotide that is an immunostimulatory non-methylated CpG-containing oligodeoxynucleotide (INO). A preferred INO is an avian Toll-like receptor (TLR) 21 agonist, such as described in WO 2012/089.800 (X4 family), WO 2012/160.183 (X43 family), or WO 2012/160.184 (X23 family).

A vaccine according to the invention can advantageously be combined with further antigenic material into a combination vaccine. However no further antigenic material derived from an avian Reovirus is required.

Therefore, in an embodiment of a vaccine according to the invention the vaccine comprises additional antigenic material that is derived from a micro-organism pathogenic to an avian, but not from an avian Reovirus.

The "additional antigenic material" may itself be in replicative or in inactivated form, or a subunit, and may be with or without an adjuvant. The additional antigenic material is derived from a further micro-organism that is pathogenic to the target avian. It may for instance comprise a biological or synthetic molecule such as a protein, a carbohydrate, a lipopolysaccharide, a nucleic acid encoding a proteinaceous antigen. Also a host cell comprising such a nucleic acid, or a live recombinant carrier micro-organism containing such a nucleic acid, may be ways to deliver the nucleic acid or the additional antigenic material to the target avian. Alternatively the additional antigenic material may comprise an inactivated micro-organism such as a parasite, bacterium or virus.

Alternatively, the vaccine according to the invention, may itself be added to a vaccine.

An advantageous effect of a combination vaccine for the invention is that it not only induces an immune response against avian Reovirus, but also against other pathogens of a target avian, while only a single handling of the target animal for the vaccination is required, thereby reducing discomfort to the target, as well as time- and labour costs.

A "micro-organism pathogenic to an avian" for the invention, is well known in the art. The additional antigenic material may therefore be derived in principle from any virus (except avian Reovirus), bacterium, parasite, fungus, rickettsia, protozoa and/or parasite that is pathogenic to an avian that is also a target for a vaccine for reducing infection by avian Reovirus according to the invention.

In a preferred embodiment a virus pathogenic to avians is selected from: infectious bronchitis virus, Newcastle disease virus, avian adenovirus, avian astrovirus, avian paramyxovirus, egg drop syndrome virus, fowl adenovirus, IBDV, chicken anaemia virus, avian encephalo-myelitis virus, fowl pox virus, turkey rhinotracheitis virus, duck plague virus, duck viral hepatitis virus, pigeon pox virus, Marek disease virus, avian leucosis virus, infectious laryngotracheitis virus, avian metapneumovirus, avian influenza virus, and goose parvovirus.

In a preferred embodiment a bacterium pathogenic to avians is selected from the bacterial genera: *Escherichia, Salmonella, Ornithobacterium, Haemophilus, Pasteurella, Bordetella, Erysipelothrix, Mycoplasma, Campylobacter, Borrelia, Enterococcus, Avibacterium, Riemerella, Listeria, Shigella, Streptococcus, Staphylococcus, Mycobacterium, Chlamydia* and *Clostridium*.

In a preferred embodiment a parasite pathogenic to avians is selected from the parasite genera: *Eimeria* and *Cryptosporidium*.

In a preferred embodiment a fungus pathogenic to avians is selected from the fungal genera: *Aspergillus* and *Candida*.

In a further aspect the invention relates to methods for the preparation of a vaccine according to the invention.

Such methods result in the availability of a vaccine according to the invention, the vaccine having the favourable effect of reducing infection by avian Reovirus in an avian, as described above.

The "preparation" of a vaccine according to the invention is carried out by means well known to the skilled person. Such methods of manufacture will in general comprise the steps of admixing and formulating antigenic material derived from an avian Reovirus for the invention with pharmaceutically acceptable excipients, followed by apportionment into appropriate sized containers. The various stages of the manufacturing process will need to be monitored by adequate tests, for instance by immunological tests for the quality and quantity of the antigens; by microbiological tests for sterility and absence of extraneous agents; and ultimately by in vitro or in vivo experiments to determine vaccine efficacy and -safety. All these are well known to a skilled person, and are prescribed in handbooks and in Governmental regulations such as the Pharmacopoeia.

A vaccine according to the invention can be prepared into a form that is suitable for administration to an avian target, and that matches with the desired route of application, and with the desired effect.

Preferably a vaccine according to the invention is formulated as an injectable liquid, such as: a suspension, solution, dispersion, or emulsion. Commonly such vaccines are prepared sterile.

In an embodiment a vaccine according to the invention is prepared from an avian Reovirus antigenic material that was inactivated. Such an inactivated avian Reovirus vaccine can now be manufactured for the invention using well known techniques.

Therefore, in a further aspect the invention relates to a method for the preparation of a vaccine according to the invention, comprising the step of inactivating avian Reovirus from each one of two genotype groups: genotype group 1 and genotype group 4.

Replicating an avian Reovirus according to the invention can be done in many ways, for example by using a host animal, and harvesting virus from blood and/or organs. However preferred is an in vitro culturing system using host cells susceptible to avian Reovirus. Such a culture system can be better monitored and controlled than production in vivo, and viral yields can be optimised. Typically an in vitro culturing system employs a culture vessel and a (semi-)defined culture medium. The host cells may be derived from an animal, yielding primary cells, or may be immortalised cells such as from an established cell-line. At small scale, the culture vessel can be a flat-bottom- or roller bottle flasks; for large scale culturing the culture vessel can be a fermenter, which also allows for several critical parameters of the culture to be monitored and adjusted when appropriate, and this can even be automated. Techniques, materials and equipment for an in vitro culture system for the invention at any scale is well known and readily available from many commercial suppliers to the life-science industry.

In an embodiment, a method for the preparation according to the invention comprises the steps of:
 a. propagating an avian Reovirus in an in vitro cell-culture,
 b. harvesting and inactivating said avian Reovirus, and
 c. admixing the inactivated avian Reovirus with a pharmaceutically acceptable carrier.

In a further embodiment, a method for the preparation according to the invention comprises the step of admixing avian Reovirus antigenic material as defined in the invention, with an adjuvant.

In further aspects the invention relates to different medical uses of the vaccine according to the invention, or of avian Reovirus antigenic material as described for the invention. These materials and methods result in the favourable effect of reducing infection by avian Reovirus in an avian, as described above.

Therefore in further aspects the invention relates to:
 A composition comprising avian Reovirus antigenic material consisting of antigenic material derived from avian Reoviruses from each one of two genotype groups: genotype group 1 and genotype group 4, for use in a vaccine for reducing infection by avian Reovirus in an avian.
 The use of avian Reovirus antigenic material consisting of antigenic material derived from avian Reoviruses from each one of two genotype groups: genotype group 1 and genotype group 4, for the manufacture of a vaccine for reducing infection by avian Reovirus in an avian.
 A vaccine according to the invention for use in reducing infection by avian Reovirus in an avian.
 The use of a vaccine according to the invention, or of a vaccine as obtainable by a method according to the invention, for reducing infection by avian Reovirus in an avian.
 A method for reducing infection by avian Reovirus in an avian, comprising the administration of a vaccine according to the invention, or of a vaccine as obtainable by a method according to the invention, to an avian.

The invention will now be further described by the following, non-limiting, examples.

EXAMPLES

1. Avian Reovirus Isolation and Sample Preparation

Avian Reovirus was isolated from chicken organs by culturing tissue homogenates on chicken embryo liver cells (CEL). In short: tissues such as tendon, liver, jejunum, and blood were obtained from (potentially) infected chickens. Blood was centrifuged and serum collected. Samples of tissues were cut out. These were placed in 6 ml tubes containing about 0.5 cc of glass beads of about 1 mm diameter, and 1 ml of phosphate buffered saline (PBS) which contained a cocktail of antibiotic- and antifungal compounds. Samples were homogenised by shaking for 20 minutes in a Mixer Mill ball mill (Retsch), followed by clarification by centrifugation. Supernatant was collected and could be stored frozen at −70° C. for later use.

Primary CEL cells were prepared fresh before use, according to a standard protocol, in short: 14-16 day old SPF chicken embryos were used to obtain livers. The livers were washed twice in PBS to remove blood, and were then incubated while stirring in a trypsin/PBS solution at 37° C. for 15 minutes. the trypsin was neutralised with FCS, and the trypsinised mixture was centrifuged for 10 min. at 600×g. The pellet was resuspended in standard growth medium (comprising a cocktail of antibiotics and 5% fetal calf serum (FCS)). This was filtered once to remove clumps, and then the CEL cells were counted and used directly.

CEL were seeded at $1.5 \times 10^6$ cells/ml in 5 ml growth medium (5% FCS) into T25 culture flasks, and incubated overnight in a moisturised incubator at 37° C. and at 5% $CO_2$, to allow establishment of a monolayer. Next day the culture medium was replaced by medium comprising 2% FCS, and the flasks were inoculated with a virus sample as 50 µl serum or tissue supernatant, next the flasks were incubated for 4-7 days After the first round of incubation, the CEL cell-layer often appeared damaged from debris, so that no distinct cytopathic effect (cpe) was visible, so a second passage was usually given: fresh CEL were prepared, seeded, and incubated as monolayer, then 50 µl of the culture supernatant from the first passage was inoculated. This was incubated for 4 days, after which avian Reovirus specific cpe (CEL cells seem to turn dark and granular, with translucent blast-like vesicles) could be clearly observed in a the flask. For cpe negative flasks a third passage could be given. Finally the culture supernatant of the 2nd or 3rd passage was harvested and stored frozen (−70° C.) for later use.

The isolates were named and numbered, whereby SL stands for ‘service laboratory’, followed by two digits for the year of isolation, a chronological isolate number, and the 2 letter code of the country of the donor material used for the isolation.

The isolated virus samples could be used directly for RNA isolation, RT-PCR and sequence analysis. The isolates that were used in animal experiments were given further treatment: samples used for challenge inoculations were amplified directly from the third round amplified isolate, to obtain higher titres and larger volumes by proliferation on CEL of CEF cells in successively larger culture vessels, such as in T75 (15 ml culture) or T175 (25 ml culture) in Cellstar™ flatbottom cell-culture flasks (Greiner Bio-One), or in 490 $cm^2$ roller bottle flasks (150 ml culture) (Corning, Fischer Scientific), all in standard culture medium and under standard culturing conditions. In this way, challenge inocula were prepared of:

- SL11A823-2 BE (genotype group 1): 7.95 Log 10 TCID50/ml
- SL11A294-12 FR (genotype group 2): 6.32 Log 10 TCID50/ml
- SL10A1581-32 ES (genotype group 3): 5.95 Log 10 TCID50/ml
- SL11A823-1 BE (genotype group 4): 7.70 Log 10 TCID50/ml Samples of avian Reovirus breakthrough isolates that were used for the preparation of vaccines were first plaque purified 3 times as described below, and then amplified in similar ways.

2. Confirmation of Virulence of Viral Isolates in Target Animals

In line with Koch's postulates, the pathogenicity and reisolation of the avian Reoviral isolates was demonstrated in experimental infections of chickens. One day old chicks were used, either from specified pathogen free (SPF) mothers, or from Reovirus vaccinated mothers. The test in these last chicks, which were positive for maternally-derived antibodies (MDA+) against classical Reovirus strains, served to confirm the vaccination-breakthrough capability of these viral isolates. Viruses used for the challenge inoculations were isolates: SL11A823-1BE, SL11A823-2BE, SL11A0294-12 FR, and SL10A1581-32 ES, that were isolated and amplified as described above. Inoculations were applied orally to mimic the natural infection route, or alternatively by intramuscular route, which had been observed to be an even more effective route of challenge-inoculation.

2.1. Experimental Design

200 Day old SPF chicks, of mixed sex, were marked using wingbands, and placed in separate negative pressure isolators, at 20 chicks per group. Chicks were White Leghorn layers, feed and water were available ad libitum, and evidently weak or small chicks were not included. In addition 10 hatchmates were bled to provide serum samples to test antibody status.

A challenge inoculation was administered the same day of placement, and in total 10 isolators were used to house the different groups: 2 isolators for each of the inoculums with avian Reovirus isolates, with one group receiving an oral and the other an intramuscular inoculation. As positive control, one isolator was added in which the chicks received a control inoculation with the live attenuated Reovirus vaccine strain 1133 by intramuscular route. Also one isolator housed a negative control group that received only a mock inoculation.

All inoculations were given in a 0.1 ml dose per chick, and at 4.5 Log 10 TCID50/chick, for both the oral and the intramuscular route. The virus-inoculum dilutions were prepared fresh and within 1 hour before administration, and were kept on ice until use. Left-over inocula were used for back-titration, to confirm the inoculum dose that had been applied.

All chicks were observed daily during the course of the experiment by qualified personnel for the occurrence of clinical signs of disease or other abnormalities. Animals showing pain or discomfort were euthanized and subjected to post-mortem examination.

Selected chicks were taken for sampling at 3 and at 10 days post inoculation, whereby blood and tissue samples were collected. From the blood, serum was obtained, half of which was used for virus re-isolation, and half for antibody determination. The various tissues (tendon, liver and jejunum) were used for homogenisation and virus reisolation.

2.2. Results of the Virulence Confirmation Experiments

The negative control chicks, or any of their samples, as well as the sera from the day zero hatchmates, did not show any signs of disease or infection that would be relevant to the experiment. Also the positive control group inoculated with avian Reovirus 1133 vaccine strain, displayed virus positive tissue—(tendon, liver) and serum samples (at 10 days p.i.) as expected, so that the experiment was valid.

Back-titration of the inoculation samples showed all inoculations were within ±0.2 Log 10 TCID50 of the intended 4.5 Log 10 TCID50 dose/chick.

2.2.1. General Observations:

Viral reisolations from blood were only positive at 3 days p.i., not at 10 days p.i.

Detection of seroresponse proved negative at 3 or 10 days p.i. for the field isolates, only isolate 1133 inoculates did become Reo antibody positive at 10 days p.i. Apparently antibody titres were not yet high enough at this time to allow detection by the commercial test for avian Reovirus antibodies used (IDEXX REO antibody Elisa).

Intramuscular inoculation caused much more samples to be positive for virus re-isolation than oral inoculation, for all of the virus isolates tested, and both at 3 and at 10 days p.i.

All field isolates were virulent both by oral and by i.m. route. Clinical signs observed were depression and growth retardation, lameness in the inoculated leg, or complete immobility. Also intestinal inflammation and liver necrosis was frequently observed. Occasionally even mortality was observed in the test animals: for the SL11A823-2 BE (genotype group 1) isolate by oral route, and for the SL10A1581-32 ES (genotype group 3) isolate by i.m. route.

While strain 1133 demonstrated a preference for tendon, the field isolates were reisolated in highest amounts from liver or jejunum; the highest reisolation overall was obtained for each of the field isolates from jejunum at 7 days p.i.

3. Nucleic Acid Isolation, Amplification and DNA-sequencing

Culture supernatant from a 2nd or 3rd isolation passage, was used to isolate total viral avian Reovirus RNA. This was used to prepare and amplify cDNA, which could then be used for DNA sequencing. Standard methods and conditions were applied for all procedures, employing commercial kits and automated laboratory equipment.

In short: viral RNA isolation was performed on 200 µl samples of culture supernatant, using the MagNA Pure™ 96 (Roche). This equipment applies lysis of the sample, and isolates nucleic acid using magnetic beads. Next, the eluted nucleic acid was used to prepare first strand cDNA, by reverse transcription with the SuperScript™ III first strand synthesis kit (Invitrogen), according to the manufacturer's instructions.

Used primers, specific for the avian Reovirus SigmaC gene were:

```
REO FW1:
                                    (SEQ ID NO: 19)
5'-AGTATTTGTGAGTACGATTG-3'

REO REV5:
                                    (SEQ ID NO: 20)
5'-GGCGCCACACCTTAGGT-3'
```

Whereby primer REO FW1 binds upstream of the SigmaC gene (approximate location on the avian Reovirus S1 genome segment: nucleotides 533-552), and primer REO REV5 binds at the 3'end of the SigmaC gene (approximate S1 segment location: 1621-1605); this makes that the penultimate downstream nucleotides of the SigmaC gene were not determined. The primer REO FW1 was used for first strand synthesis, and both primers FW1 and REV5 were used for PCR amplification and sequencing reactions. These primers could be used for avian Reovirus samples from all genotype groups, however, occasionally the reverse primer was not effective enough, so that for some avian Reovirus samples additional primers were designed and used, to further amplify the viral nucleic acid.

After cDNA synthesis, samples were amplified by PCR, using the FW1 and REV5 primers at 0.4 µM final concentration in 50 µl samples with 2 µl cDNA sample, using the Phusion™ High-Fidelity DNA polymerase and master mix (Thermo Scientific). PCR conditions used were: 60 sec. 98° C.; 35 cycles of: 10 sec. 98° C., 30 sec. of 58° C., and 30 sec. 72° C.; followed by 10 min. at 72° C.

cDNA preparation was verified by agarose gel-electrophoresis on a 1% agarose gel (Hispanagar), containing ethidium bromide, and by comparison to a Smartladder™ (Eurogentec) 200-10.000 bp marker lane. Gel bands of about 1.1 kbp were routinely obtained, illustrative of successful avian Reovirus SigmaC gene amplification.

PCR samples positive for a 1088 bp band were purified using the QIAquick™ PCR purification kit (Qiagen). Next the DNA concentration was measured in a NanoDrop™ spectrophotometer (Thermo Scientific). Typically between 10 and 40 ng/µl of viral cDNA was obtained.

DNA sequence determination was done using automated cycle-sequencing equipment and sequence readings were assembled, aligned and analysed using computer software, all according to the manufacturer's instructions. In short: first cycle sequencing PCR was performed with 20 to 70 ng viral cDNA (typically 1 or 2 µl of the purified PCR amplified viral cDNA sample), and 0.5 µM of the FW1 or REV5 primer in 20 µl per reaction, using the Big Dye™ Terminator Cycle Sequencing kit (Applied Biosystems). The sequencing PCR program was: 25 cycles of: 10 sec. 96° C., 5 sec. 50° C., and 2 min. 60° C. Next, samples were kept at 15° C. until analysis.

Next the sequencing-PCR samples were purified using the Dye Ex™ Spin kit (Qiagen) according to the manufacturer's instructions, and samples were stored at 4° C. until the sequencing run commenced.

DNA sequencing was performed by capillary electrophoresis using an ABI 3500 Genetic Analyzer™ and corresponding software (Applied Biosystems). Sequence data was then analysed using Sequencher™ v.54 software (Gene Codes Corp.).

Some ambiguities in the assembled sequences could be resolved by use of additional primers, hybridising to internal regions of the SigmaC gene, to provide additional overlapping readings.

4. Sequence Alignments and Phylogeny

Avian Reovirus amino acid sequences of SigmaC protein were analysed, both from sequenced field isolates as described above, and from public databases. The amino acid sequences were aligned using a combination of programs, such as: SIAS (http://imed.med.ucm.es/Tools/sias.html) for multiple pairwise sequence alignments, and MEGA6 (supra) for collection of results and phylogeny. Alignments were verified by one-on-one alignments using BlastP (supra), and the scores from this program were decisive in attributing a genotype group to a viral sequence.

In several of the avian Reovirus outbreak isolates, the last 30 or so nucleic acids of the 3' region of the gene encoding the sigmaC protein could not be determined with confidence, as these bases directly followed the downstream PCR primer. Also, for several of the sequences from the public databases information on the C-terminal end of the sigmaC protein was missing. So to optimise the overlap in the alignments, the C-terminal end of the sigmaC protein's amino acid sequence was not used in these analyses. However this did not seem to affect the fidelity of the grouping, as Kant et al. (supra) had also noted: using less than a complete sigmaC protein's amino acid sequence still could provide reliable grouping. Similarly, an occasional sequence ambiguity did not hinder the analysis.

Alignments were made using amino acids 1-277 of the SigmaC protein when possible; sequences that were much shorter were not included in the analyses. An slightly shorter sequence, such as ISR-5223 was still included as this provided a link to prior art type genotype grouping.

The alignment scores were rounded-off to whole integers, in line with the score results as provided by the BLAST program. However this means these numbers are accurate up to 0.49%, which over a length of 277 amino acids corresponds to 2 amino acids.

Tables describing the various sequences analysed, and their grouping are given in the Tables section below, and a graphical representations of the phylogeny of the five genotype groups are presented in the Figures. From the many field sample tested, only a selected number of relevant and representative samples are reproduced here: Table 1 describes the most relevant of these field samples, and a further selection was made for those for which the full amino acid sequence is presented in the attached sequence listing, see Table 2. In Table 3 are listed the most relevant of the publicly available sequences, with their corresponding Database accession numbers, and their prior genotype grouping.

Table 4 presents—in several sections—the results of pairwise multiple alignments of avian Reovirus SigmaC amino acid sequences for the different genotype groups; the amino acid sequence of the genotype group's reference strain was aligned to the listed sequences. The results are in percent amino acid identity, and are presented for representative members of the genotype (sub)group, as well as for the reference strains of the other genotype groups. From these alignments, the cut-off values were deducted that serve to characterise the different genotype groups as defined herein.

5. Plaque Purification of Field-isolates

For two of the avian Reovirus breakthrough strains, plaque isolation was performed to obtain a clonally pure viral isolate for vaccination studies. These were isolates: SL11A823-1 BE, and: SL11A823-2BE, respectively belonging to genotype groups: 4 and 1. This was done using standard isolation of viral plaques on CEL cells in tissue culture dishes under agar. In short: dilutions were prepared of the two virus isolates, up to $1\times10^{\wedge}8$. Next 6 cm diameter cell-culture dishes were inoculated with 1 ml of CEL cells at $5\times10^{\wedge}6$ cells/ml, 1 ml viral dilution, and 3 ml standard growth medium with FCS and antibiotics. The dishes were incubated O/N. The next day supernatant medium was discarded, and the monolayer was washed twice with PBS. Next the dishes were given a 5 ml agarose overlay of a 1:1 mixture of: bacto agar dissolved at 2.25% in distilled water at 49° C., and 2× culture medium at 37° C. Dishes were incubated for 4 days, and stained with neutral red: each dish was given 2 ml of a solution of 0.04% v/v neutral red in PBS. This was incubated for 6 hours, after which viral plaques were visible.

For each viral isolate, several individual plaques were picked from a dish with clearly separated plaques from high dilutions. The plaques were taken up into 0.5 ml of PBS. Next each plaque isolate was given one round of amplification on CEL cells in a T25 culture flask.

The plaque isolations were repeated for two more rounds using 0.1 ml of the plaque amplificate from the previous round, to a total of three rounds of plaque purification; negative control dishes and flasks were always included.

The 3rd round plaque purified avian Reovirus isolates were then amplified on primary chicken embryo fibroblast cells (CEF) in larger tissue culture flasks; CEF cells were prepared essentially in the same way as CEL cells, except that whole embryos were used for the trypsinisation. The amplifications yielded large volumes of high titred virus stocks for further use; titres of 7-8 Log 10 TCID50/ml could routinely be obtained.

6. Vaccine Preparation

The plaque purified avian Reovirus isolates were further amplified for the production of experimental vaccines. To this purpose the viruses were propagated on Vero cells, the culture supernatants were harvested, inactivated with formaldehyde, and the inactivated viral antigen was used for emulsification with a mineral oil adjuvant into a water-in-oil emulsion vaccine. In short: a suspension of Vero cells at $1\times10^{\wedge}5$ cells/ml was seeded into 1750 cm$^2$ rollerbottles with 500 ml of standard growth medium with 5% FCS and antibiotics. The rollerbottles were inoculated with 1 ml of the amplified plaque purified avian Reovirus isolates SL11A823-1BE or SL11A823-2BE, and incubated at 37° C. while rolling.

After 5-6 days 100% cpe was observed, and the culture-supernatant was harvested. Diluted formalin was added to the culture-supernatant to a final concentration of 0.2% v/v. This mixture was left to inactivate for 48 hours at 37° C., while stirring at 200 rpm.

After the inactivation, the avian Reovirus antigens were concentrated about 20 fold by ultra-filtration. At the laboratory scale this was performed using a Centriprep™ centrifugal filter device (Millipore) with a 10 kDa cut-off membrane: 15 ml volume samples were centrifuge for 40 minutes at 3000×g at 20° C. The concentrated viral antigen was stored refrigerated at 2-8° C. until further use.

An adjuvated vaccine was prepared by combining the avian Reovirus antigenic materials with an oily phase. The watery phase had been prepared by stirring aseptically water-for-injection with the concentrated viral antigen. The oily phase contained liquid paraffin as mineral oil and emulsifiers which (at the laboratory scale) were homogenised with the oil using an Ultra Turrax™ (IKA), next the oily phase was filter-sterilised through a 0.2 μm Ultipor™ nylon filter (Pall). The oily and the watery phases were then emulsified using an Ultra Turrax, in runs of a few minutes to avoid heating up the mixture over 40° C. Homogeneity was then checked by light-microscopy. This was repeated until all water vesicles were smaller than 3 μm.

Next, the ready vaccine was dispensed into labelled sterile bottles under aseptic conditions, the bottles were closed with nitryl rubber stoppers, and sealed with a coded aluminium cap. The final vaccine product was stored refrigerated until use.

In this way, avian Reovirus vaccines according to the invention were prepared. For a vaccine dose of 0.5 ml per chicken, the vaccine was made to contain 1% v/v per ml (over the final volume of the emulsified vaccine) of viral antigen of SL11A823-1BE (at 8.32 Log 10 TCID50/ml), and 2% v/v of SL11A823-2BE (at 6.45 Log 10 TCID50/ml). Control vaccines contained either no viral antigen, or only one of these two viral antigens.

Similar vaccines were prepared to serve as comparative examples, containing other avian Reovirus antigens: either 'classical' vaccine strains 1733 and 2408, as a multimeric single genotype group vaccine; or a combination of strains 1733, 2408 and ERS, containing antigens from genotype groups 1 (in two fold) and 5. The amounts of antigen used for these comparative vaccines were the same as in current commercial vaccines, and were measured in arbitrary Elisa units against a known standard reference.

7. Vaccination-challenge Experiments

The water-in-oil vaccines prepared as described above were used in animal vaccination-challenge trials. In a series of experiments layer chickens were vaccinated with a vaccine according to the invention, based on avian Reovirus antigenic material from genotype groups 1 and 4, while their progeny was subjected by challenge inoculation to a severe infection with avian Reovirus from different genotype groups, to demonstrate the broad-spectrum protective- and cross-protective properties of such vaccines, to homologous- and heterologous challenge virus infection.

7.1. Experimental Design 7.1.1. Parental Vaccination

Normal healthy SPF layer chickens were assigned to 8 groups of 12 chickens each. The chickens were White Leghorn layers, about 32 weeks of age, and to each group of 12 hens one rooster was added.

The hens were vaccinated with one dose (0.5 ml) of the water-in-oil vaccine as described above, intramuscularly in the right breast muscle. The roosters were not vaccinated to provide negative control serum samples. From five weeks after vaccination eggs were collected daily for the subsequent challenge-inoculation experiments on the progeny. The eggs were stored at 4° C. until use.

All chickens were housed in containment facilities, with Hepa filtered air in- and outlets. Standard chicken feed and tap water were available ad libitum.

Chickens were assigned to the groups as they came to hand, although each group of hens was provided with one rooster. Chickens were marked individually using wing-bands or swift-tags.

All chickens were placed one week prior to vaccination for acclimatisation, and were observed daily during the course of the experiment by qualified personnel for the occurrence of clinical signs of disease or other abnormalities.

Parent Vaccination Schedule:
Group 1: vaccine: SL11A823-1BE antigen
Group 2: vaccine: SL11A823-2BE antigen
Group 3: vaccine: SL11A823-1BE antigen and SL11A823-2BE antigen
Group 4: mock vaccine (not containing avian Reovirus antigen)
Group 5: 'classic' avian Reovirus vaccine: 'strains 1733 and 2408 antigens (vaccine similar to the commercial vaccine Nobilis® Reo Inac).
Group 6: 'classic' avian Reovirus vaccine (strains 1733 and 2408 antigens) with strain ERS antigen
Roosters: no vaccine 7.1.2. Offspring Challenge Inoculation This experiment served to test the protection in progeny from vaccinated parents, for their ability to overcome a severe avian Reovirus infection, even when the challenge virus was from a different genotype group then the vaccine virus. Because of the scale and size, this was performed in two consecutive experiments, one testing challenge inoculation with isolates SL11A294-12 FR (genotype group 2) and SL10A1581-32 ES (genotype group 3), and two weeks later on new progeny from the same parents, a further series of challenge inoculations using isolates: SL11A823-1 BE (genotype group 4), and SL11A823-2 BE (genotype group 1).

For both of these experiments, eggs collected from the parental vaccination experiment were incubated—divided by their parental treatment groups—in standard hatching incubators upto hatch at day 21. The day old chicks (of mixed sex) were gathered and were marked using wing-bands. Evidently weak or small chicks were not included. From each parental treatment group 10 chicks were bled to provide serum samples to test the chicks' initial MDA status. Then chicks were divided by placement in separate negative pressure isolators, so that from each parental treatment group there was one isolator, containing 24-30 chicks. Feed and water were available ad libitum.

The challenge inoculation was administered at the same day of placement: per isolator one type of challenge virus was used, whereby half of the chicks received the challenge by oral route and the other half by intramuscular route. Chicks were bled for collection of blood samples at 3 or at 10 days p.i.

The challenge inoculations were given in a 0.1 ml dose with 4.5 Log 10 TCID50/chick, for each of the four challenge viruses tested, and was inoculated via the intramuscular (i.m.) route. The challenge virus dilutions were prepared fresh and within 1 hour before administration, and were kept on ice until use. Left-over inocula were used for back-titration, to confirm the inoculum dose that had been applied.

All chicks were observed daily during the course of the experiment by qualified personnel for the occurrence of clinical signs of disease or other abnormalities. Animals showing pain or discomfort were euthanized and subjected to post-mortem examination.

7.2. Sample Analyses

From the parents, blood samples were taken at 2 and 4 weeks after vaccination, as well as at 1 week before vaccination (day 0). From the offspring blood samples were taken at the start of the experiment and at 3 or 10 days p.i.

The blood samples were transported to the laboratory at ambient temperature. After clotting at room temperature, serum was collected. For the progeny: half of the serum was stored at −70° C. for virus-isolation; remaining serum samples were heat inactivated for 30 minutes at 56° C., and subsequently, stored at −20° C. until use.

The detection of avian Reovirus antibodies in the serum was done using the IDEXX REO antibody Elisa, according to the manufacturer's instructions.

The experiments' validity was determined based on the absence of antibodies in the parents against avian Reovirus in the day 0 samples, and in the negative control samples.

Offspring from the vaccinated hens was MDA+ against avian Reovirus, depending on their parents' treatment.

Serum for virus reisolation had been obtained after clotting of the blood sample, and this was frozen at −70° C. without further treatment. When testing these samples, CEL cells had been seeded into 6 well tissue culture plates, at 2 ml per well with $1\times10^6$ cells/ml, in standard culture medium with 5% FCS and antibiotics. This was incubated overnight to form a monolayer. Next day the culture supernatant was removed and replaced with 4 ml standard medium without FCS. The wells were inoculated with 40 μl of the test serum, and incubated for 5 days. Then 100 μl of the well's supernatant was inoculated into wells of a new 6 well plate with CEL monolayer, and incubated again for 5 days. Next, avian Reovirus specific cpe was judged by light-microscopy. As negative samples remained negative even after a third passage, the two passages were used as standard.

7.3. Results of the Vaccination-challenge Experiments 7.3.1. Controls

As all positive and negative control samples scored as was expected, therefore the experiment was considered valid.

7.3.2. Method of Assessing Results

In assessing the results of the experiments on parent vaccination and offspring challenge, the many samples collected over the course of the experiment were analysed and compared. Serum was obtained and tested for antibodies and for virus reisolation; as for serology the 3-10 day measuring period was found not to be long enough to give clear positive results. Positive virus reisolation from serum was an indicator for an active avian Reovirus viraemia, and it was found that the virus reisolation from serum collected at 3 days after the intramuscular inoculation, gave a clear picture of the effect of the different treatments. This way it could be determined which vaccination of the parent could reduce the infection of avian Reovirus challenge virus in the progeny.

For the treatment group receiving i.m. challenge, and serum collected at 3 days p.i., the serum from 5 chicks (one group only 4) per group were available for virus reisolation. As a cut-off, groups having 3 or more animals positive for virus reisolation in serum taken at 3 days p.i., were considered not to show reduction of challenge virus infection; 2 animals positive was considered doubtful; and zero or 1 positive was considered to show reduction of infection. Results are shown in Table 5, displaying if (YES), or if not (NO) reduction of infection by avian Reovirus challenge strain in the progeny was induced by the different vaccinations of the parents. Between brackets is indicated the basis for that conclusion by the number of chicks of the total tested, for which the serum sample taken at 3 d. p.i. was positive for avian Reovirus as determined by reading cpe after two passages on CEL cells.

7.3.3. Discussion of Results

As is presented in Table 5, for all chicks derived from mock vaccinated parents (vaccination test group 4), avian Reovirus could be reisolated from serum taken at day 3 after inoculation, and this was the case for all of the challenge viruses applied. This indicated that the challenge virus had replicated unhindered in the chicks, and consequently that the chicks had not been protected by factors transferred from their (mock vaccinated) parents. Clinical signs were not overly apparent, as the chickens used here were of layer type, which are less sensitive than heavier type chickens such as broilers. Nevertheless clear differences in vaccination efficacy were observed.

Parents in test group 5 were given a single vaccination with a vaccine containing antigenic material from two strains of 'classic' avian Reovirus: strains 1733 and 2408, to mimic a broad genotype group 1 vaccine. This vaccine induced in offspring a significant reduction of infection by avian Reovirus challenge virus belonging to genotype groups 1 or 2 as defined herein. However no reduction of infection was induced against avian Reovirus challenge virus of genotype groups 3 or 4.

Remarkably, parents in test group 6 did not provide a protection to their offspring that was any broader than that already provided by the genotype group 1 antigenic material as used for the vaccination of test group 5. This even though the vaccine used for group 6 had additional avian Reovirus antigenic material: from ERS strain (ERS strain belonging to genotype group 5 as defined herein). This shows that apparently there is no automatic broadening of protection obtained from the use of vaccines containing avian Reovirus antigenic material from more than a single genotype group.

The vaccines used for test groups 1 or 2 contained antigenic material of avian Reovirus from either genotype group 1 or 4 (respectively). The parents from these test groups provided total protection in their offspring against the replication of avian Reovirus challenge virus that was of the same genotype as the vaccine strain. However no broad-spectrum or heterologous protection was induced, as these vaccines did not reduce infection by avian Reovirus from a genotype group that was different from their own genotype group.

However, surprisingly it was found that a strong synergistic effect was obtained upon the combination of avian Reovirus antigenic material from genotype groups 1 and 4: parents receiving the vaccine of test group 3, which combined antigenic material from avian Reovirus genotype groups 1 and 4 (as defined herein) did provide broad-spectrum protection to their offspring: the chicks from these parents were able to reduce significantly the infection of all avian Reovirus challenge strains tested, both homologous and heterologous to the vaccine applied, and after a single vaccination.

Tables

TABLE 1

List of avian Reovirus field-outbreak isolates mentioned in the Examples

| Sample name | Isolation year | Country | Genotype group |
|---|---|---|---|
| SL06A0161-4 | 2006 | US | 4 |
| SL06A0161-5 | 2006 | US | 4 |
| SL09A0324-2 | 2009 | DE | 2 |
| SL09A0324-3 | 2009 | DE | 2 |
| SL09A0417-1 | 2009 | BE | 2 |
| SL09A0459-11 | 2009 | DK | 4 |
| SL09A0531-1 | 2009 | PL | 5 |
| SL09A0877-4 | 2009 | UK | 3 |
| SL09A0905-7 | 2009 | DK | 4 |
| SL09A1218-3 | 2009 | FR | 4 |
| SL10A0282-8 | 2010 | LT | 1 B |
| SL10A0822-2 | 2010 | UK | 1 B |
| SL10A1581-32 | 2010 | ES | 3 |
| SL10A1597-4 | 2010 | NL | 1 B |
| SL11A0268-12 | 2011 | FR | 2 |
| SL11A0294-12 | 2011 | FR | 2 |
| SL11A0712-12 | 2011 | HU | 3 |
| SL11A0823-1 | 2011 | BE | 4 |
| SL11A0823-2 | 2011 | BE | 1 B |
| SL11A1174-2 | 2011 | FR | 4 |
| SL11A1179-3 | 2011 | FR | 1 B |
| SL11A1192-1 | 2011 | LV | 4 |
| SL11A1414-13 | 2011 | FR | 5 |
| SL11A1417-1 | 2011 | BE | 1 B |
| SL11A1539-1 | 2011 | NL | 4 |
| SL11A1646-41 | 2011 | FR | 5 |
| SL11A1646-43 | 2011 | FR | 5 |
| SL12A1142-1 | 2012 | FR | 1 B |
| SL12A1627-4 | 2012 | FR | 1 B |
| SL12A1628-1 | 2012 | FR | 1 B |
| SL13A0226-1 | 2013 | UK | 1 B |
| SL13A0226-2 | 2013 | UK | 4 |
| SL13A0988-1 | 2013 | BE | 2 |
| SL13A0988-2 | 2013 | BE | 1 B |
| SL13A1000-5 | 2013 | UK | 1 B |
| SL13A1000-6 | 2013 | UK | 1 B |

TABLE 2

Description of sequences presented in the sequence listing

| SEQ ID NO: | name | genotype group |
|---|---|---|
| 1 | SL11A0823-2_BE | 1B |
| 2 | SL11A0294-12_FR | 2 |
| 3 | SL10A1581-32_ES | 3 |
| 4 | SL11A0823-1_BE | 4 |
| 5 | ERS | 5 |
| 6 | Reo-2177 | 1A |
| 7 | SL11A1417-1_BE | 1B |
| 8 | SL10A0282-8_LT | 1B |
| 9 | SL09A0324-2_DE | 2 |
| 10 | SL13A0988-1_BE | 2 |
| 11 | SL09A0417-1_BE | 2 |
| 12 | SL11A0712-12_HU | 3 |
| 13 | SL09A0877-4_UK | 3 |
| 14 | SL11A1539-1_NL | 4 |
| 15 | SL11A1192-1_LV | 4 |
| 16 | SL09A1218-3_FR | 4 |
| 17 | SL09A0531-1_PL | 5 |
| 18 | SL11A1646-43_FR | 5 |
| 19 | PCR primer: REO FW1 | |
| 20 | PCR primer: REO REV5 | |

TABLE 3

List of avian Reoviruses from prior art, mentioned in the Examples

| Reovirus name | Year of isolation | Country | GenBank acc. nr. or SEQ ID NO | Genotype group | Prior classification |
|---|---|---|---|---|---|
| 138 | 1992 | US | AF218359 | 1 A | Kant, grp. 1 |
| 916 | 1992 | TW | AF297214 | 2 | Kant, grp. 2 |
| 919 | 1992 | TW | AF204949 | 1 A | Kant, grp. 1 |
| 1133 | 1973 | US | DQ868790 | 1 A | |
| 1733 | 1983 | US | AAB61607 | 1 A | classic vaccine strains; |
| 2177 | 1983 | US | SEQ ID NO: 6 | 1 A | Kant, grp. 1; Lublin grp. 4 |
| 2408 | 1983 | US | AF204945 | 1 A | |
| 40973/2005 | 2005 | US | DQ872797 | 4 | |
| 41560/2005 | 2005 | US | DQ872798 | 2 | |
| 41565/2005 | 2005 | US | DQ872799 | 3 | |
| 42563-1/2005 | 2005 | US | DQ872800 | 2 | |
| 42563-4/2005 | 2005 | US | DQ872801 | 3 | Kant, grp. 3 |
| AVS-B | 2006 | US | FR694197 | 4 | Kant, grp. 4 |
| ERS | 1999 | PL | SEQ ID NO: 5 | 5 | |
| GEL01 96T | 1996 | DE | AF354221 | 4 | Kant, grp. 4 |
| GEI10 97M | 1997 | DE | AF354219 | 5 | Kant, grp. 5; Lublin grp. 2 |
| GEL05 96M | 1996 | DE | AF354223 | 4 | |
| GEL06 97M | 1997 | DE | AF354224 | 1 B | Kant, grp. 1; Lublin, grp. 1 |
| GEL12 98M | 1998 | DE | AF354225 | 1 B | |
| GEL13A 98M | 1998 | DE | AF354226 | 2 | Kant, grp. 2; Lublin grp. 3 |
| GEL13B 98M | 1998 | DE | AF354227 | 3 | Kant, grp. 3 |
| ISR5215 | 2005/7 | IL | FJ793531 | 1 B | Kant, grp. 1; Lublin, grp. 1 |
| ISR5223 | 2005/7 | IL | FJ793544 | 5 | Kant, grp. 5; Lublin, grp. 2 |
| ISR59103 | 2005/7 | IL | AY332520 | 1 A | Lublin, grp. 4 |
| NLI12 96M | 1996 | NL | AF354230 | 4 | Kant, grp. 4 |
| RAM1 | 1971 | AU | L38502 | 5 | Kant, grp. 5 |
| Som4 | 1971 | AU | L07069 | 5 | Kant, grp. 5 |
| VA-1 | 1984 | IN | EU681254 | 1 A | |

TABLE 4

Pairwise multiple alignments of avian Reovirus SigmaC amino acid sequences.

Genotype group 1; Subgroup 1 A

| | Reference sequence: Reo-1733 | score |
|---|---|---|
| Group members | Reo-138 | 83% |
| | Reo-2177 | 95% |
| | VA-1 | 97% |
| | GenBank_KC963051.1_CHINA | 98% |
| | ISR59103 | 99% |
| | GenBank_KC963052.1_CHINA | 99% |
| | Reo-919 | 99% |
| | Reo-1133 | 100% |
| | Reo-2408 | 100% |

| Reference strains, other groups | Genotype Group | | |
|---|---|---|---|
| | 1B | SL11A0823-2_BE | 75% |
| | 2 | SL11A0294-12_FR | 55% |
| | 3 | SL10A1581-32_ES | 52% |
| | 4 | SL11A0823-1_BE | 49% |
| | 5 | ERS | 48% |

Genotype group 1; Subgroup 1 B

| | Reference sequence: SL11A0823-2_BE | score |
|---|---|---|
| Group members | SL11A1417-1_BE | 83% |
| | GEL12_98M | 85% |
| | GEL06_97M | 87% |
| | ISR5215 | 88% |
| | SL13A0988-2_BE | 90% |
| | SL13A0226-1_UK | 92% |
| | SL10A0282-8_LT | 92% |
| | SL13A1000-6_UK | 92% |
| | SL10A0822-2_UK | 93% |
| | SL11A1179-3_FR | 94% |
| | SL10A1597-4_NL | 94% |
| | SL12A1627-4_FR | 96% |

TABLE 4-continued

Pairwise multiple alignments of avian Reovirus SigmaC amino acid sequences.

|  |  |  |  |
|---|---|---|---|
|  | GenBank_HE985297.1_FR | 96% |  |
|  | SL12A1142-1_FR | 96% |  |
|  | SL12A1628-1_FR | 96% |  |
|  | GenBank_HE985300.1_FR | 97% |  |
|  | SL13A1000-5_UK | 97% |  |

| Reference strains, other groups | Genotype Group |  |  |
|---|---|---|---|
|  | 1A | Reo-1733 | 75% |
|  | 2 | SL11A0294-12_FR | 55% |
|  | 3 | SL10A1581-32_ES | 50% |
|  | 4 | SL11A0823-1_BE | 51% |
|  | 5 | ERS | 49% |

Genotype group 2

| Reference sequence: SL11A0294-12_FR |  | score |
|---|---|---|
| Group members | Reo-916 | 59% |
|  | GenBank_JX983602.1_USA-GA | 68% |
|  | SL09A0324-2_DE | 69% |
|  | GenBank_JX983599.1_USA-GA | 69% |
|  | Reo-42563-1/2005 | 69% |
|  | GEL13a_98M | 70% |
|  | SL13A0988-1_BE | 70% |
|  | Reo-41560/2005 | 71% |
|  | SL09A0417-1_BE | 81% |
|  | SL09A0324-3_DE | 91% |
|  | SL11A0268-12_FR | 96% |

| Reference strains, other groups | Genotype Group |  |  |
|---|---|---|---|
|  | 1A | Reo-1733 | 55% |
|  | 1B | SL11A0823-2_BE | 55% |
|  | 3 | SL10A1581-32_ES | 48% |
|  | 4 | SL11A0823-1_BE | 52% |
|  | 5 | ERS | 48% |

Genotype group 3

| Reference sequence: SL10A1581-32_ES |  | score |
|---|---|---|
| Group members | GEL13B98M | 61% |
|  | Reo-42563-4/2005 | 61% |
|  | Reo-40963/2005 | 63% |
|  | SL11A0712-12_HU | 63% |
|  | Reo-41565/2005 | 65% |
|  | SL09A0877-4_UK | 90% |

| Reference strains, other groups | Genotype Group |  |  |
|---|---|---|---|
|  | 1A | Reo-1733 | 52% |
|  | 1B | SL11A0823-2_BE | 50% |
|  | 2 | SL11A0294-12_FR | 48% |
|  | 4 | SL11A0823-1_BE | 53% |
|  | 5 | ERS | 50% |

Genotype group 4

| Reference sequence: SL11A0823-1_BE |  | score |
|---|---|---|
| Group members | SL11A1539-1_NL | 66% |
|  | SL13A0226-2_UK | 66% |
|  | GenBank_JX983600.1_USA-GA | 67% |
|  | SL11A1192-1_LV | 67% |
|  | SL06A0161-4_USA | 67% |
|  | SL11A1174-2_FR | 67% |
|  | SL06A0161-5_USA | 68% |
|  | AVS-B | 68% |
|  | SL09A1218-3_FR | 68% |
|  | Reo-40973/2005 | 68% |
|  | GEL01_96T | 92% |
|  | GEL05_96M | 97% |
|  | NLI12_96M | 97% |
|  | SL09A0905-7_DK | 97% |
|  | SL09A0459-11_DK | 98% |

| Reference strains, other groups | Genotype Group |  |  |
|---|---|---|---|
|  | 1A | Reo-1733 | 49% |
|  | 1B | SL11A0823-2_BE | 51% |
|  | 2 | SL11A0294-12_FR | 52% |
|  | 3 | SL10A1581-32_ES | 53% |
|  | 5 | ERS | 64% |

Genotype group 5

| Reference sequence: ERS |  | score |
|---|---|---|
| Group members | ISR5223 | 74% |
|  | SL09A0531-1_PL | 78% |
|  | GEI10_97M | 80% |
|  | SL11A1646-43_FR | 80% |
|  | SL11A1414-13_FR | 81% |
|  | Som4 | 82% |
|  | RAMI | 82% |
|  | SL11A1646-41_FR | 83% |

| Reference strains, other groups | Genotype Group |  |  |
|---|---|---|---|
|  | 1A | Reo-1733 | 48% |
|  | 1B | SL11A0823-2_BE | 49% |
|  | 2 | SL11A0294-12_FR | 48% |
|  | 3 | SL10A1581-32_ES | 50% |
|  | 4 | SL11A0823-1_BE | 64% |

TABLE 5

Results of vaccination - challenge experiments

Reduction of infection in progeny by different avian Reovirus challenge strains
(No. of chicks per total positive for Reovirus (cpe) in serum at 3 d. p.i.)

| Group | Parental vaccine | SL11A823-2 BE (genotype group 1) | SL11A294-12 FR (genotype group 2) | SL10A1581-32 ES (genotype group 3) | SL11A823-1 BE (genotype group 4) |
|---|---|---|---|---|---|
| 1 | SL11A823-1 BE (genotype group 4) | NO (3/5) | n.d. | n.d. | YES (0/5) |
| 2 | SL11A823-2 BE (genotype group 1) | YES (0/5) | n.d. | n.d. | NO (3/5) |
| 3 | 823-1 + 823-2 (genotype groups 4 + 1) | YES (1/5) | YES (0/4) | YES (1/5) | YES (0/5) |
| 4 | mock vaccine | NO (5/5) | NO (5/5) | NO (5/5) | NO (5/5) |

TABLE 5-continued

Results of vaccination - challenge experiments

| | | Reduction of infection in progeny by different avian Reovirus challenge strains (No. of chicks per total positive for Reovirus (cpe) in serum at 3 d. p.i.) | | | |
|---|---|---|---|---|---|
| Group | Parental vaccine | SL11A823-2 BE (genotype group 1) | SL11A294-12 FR (genotype group 2) | SL10A1581-32 ES (genotype group 3) | SL11A823-1 BE (genotype group 4) |
| 5 | 1733 + 2408 (genotype group 1) | YES (1/5) | YES (0/5) | NO (3/5) | NO (4/5) |
| 6 | 1733 + 2408 + ERS (genotype groups 1 and 5) | YES (0/5) | YES (1/5) | NO (5/5) | NO (3/5) | n.d. = not done

LEGEND TO THE FIGURES

FIGS. 1-6:

Phylogenetic trees of amino acid sequence alignments from sigmaC proteins of representative avian Reoviruses that were analysed and compared in the Examples, for all the genotype (sub)groups. The trees were drawn using MEGA6, by first calculating pairwise alignment scores, and then drawing unrooted trees using the neighbour-joining method (Saitou N. & Nei M., 1987, Mol. Biol. and Evol., vol. 4, p. 406-425). The scale bar indicates the relative genetic distance.

Figure 2:
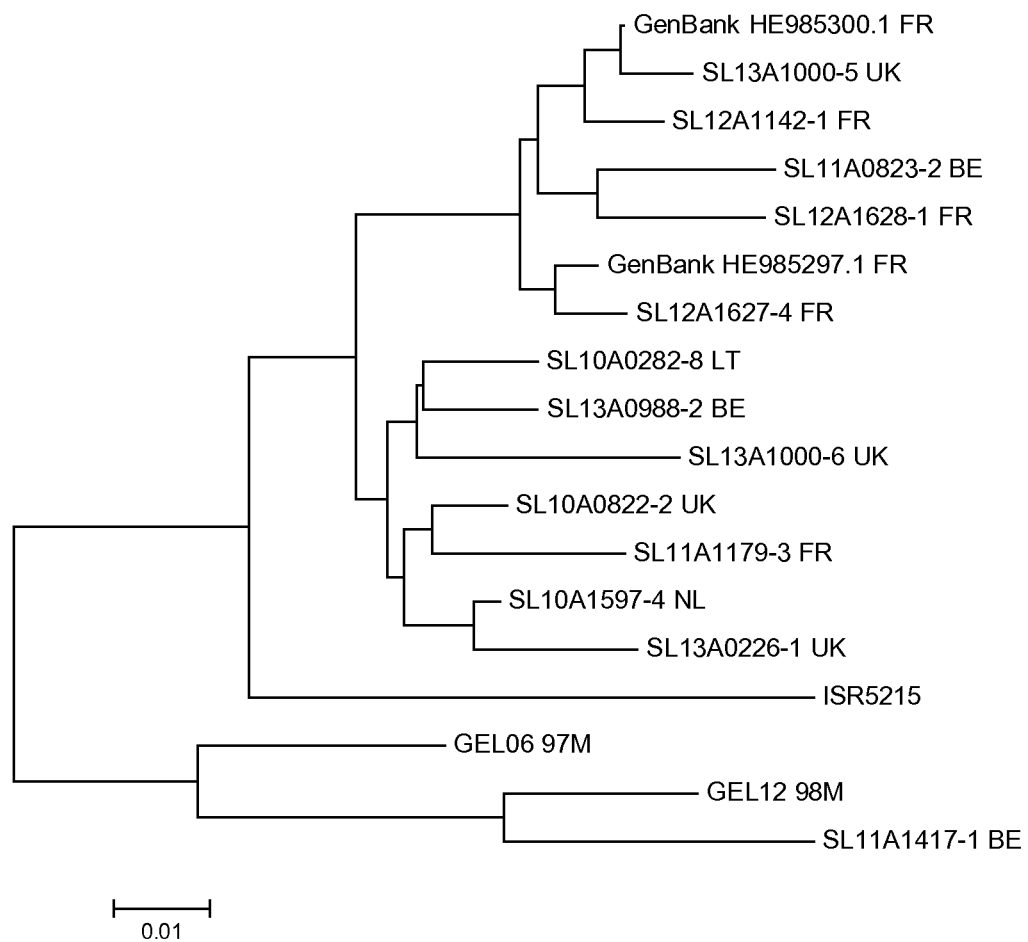
Figure 3:
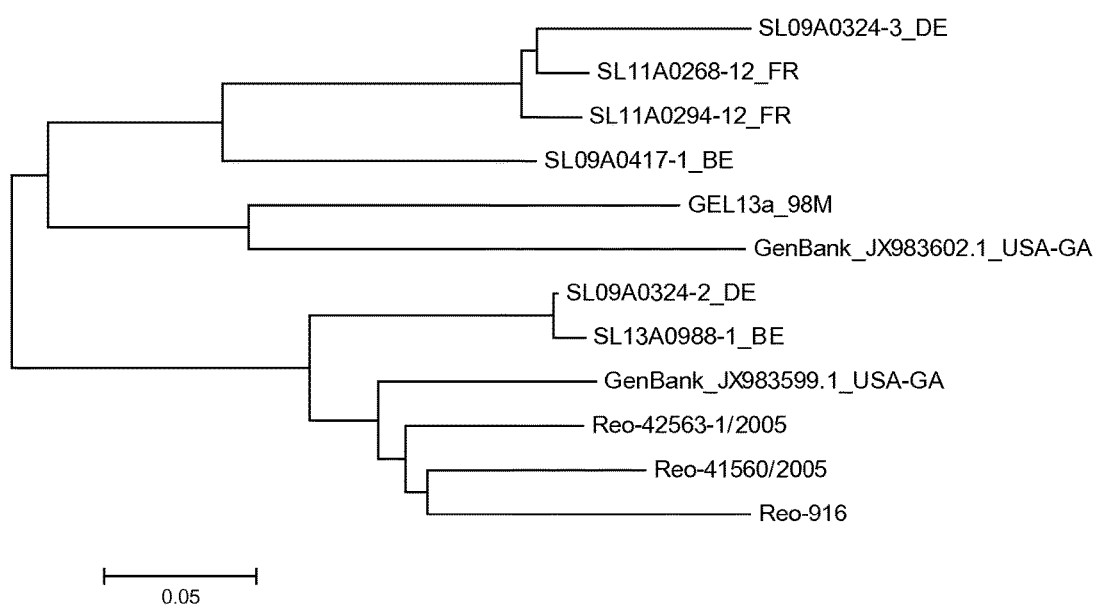
Figure 4:
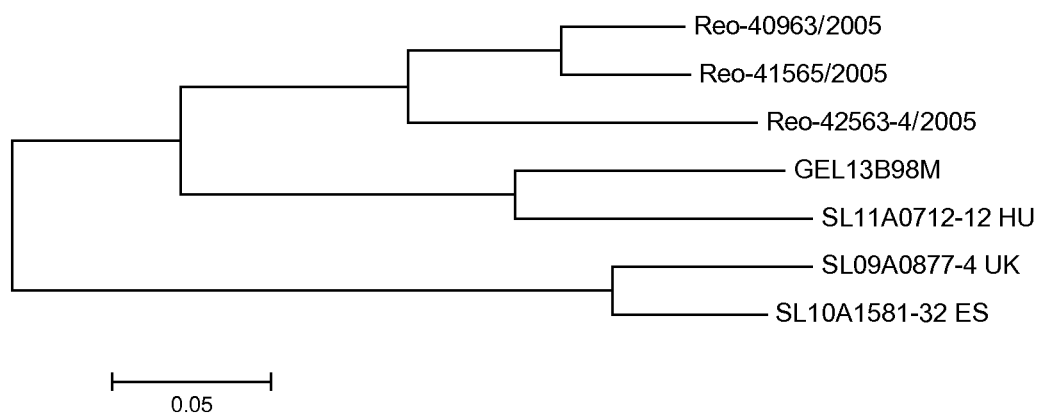
Figure 5:
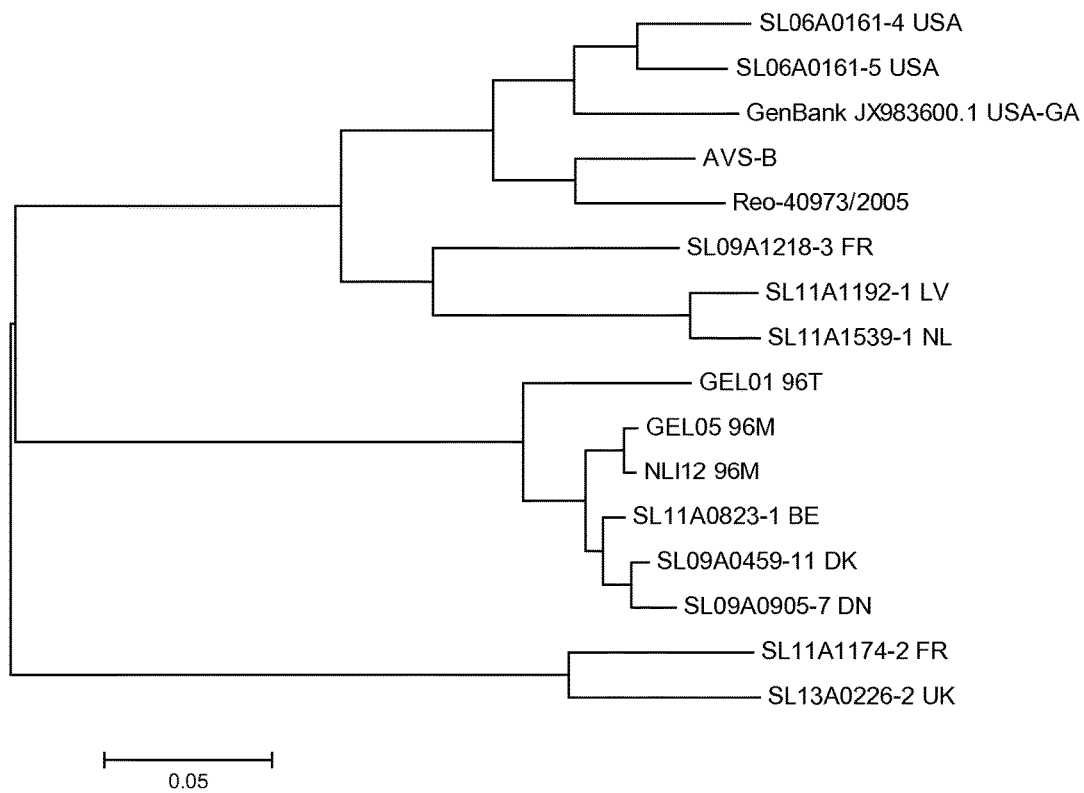
Figure 6:
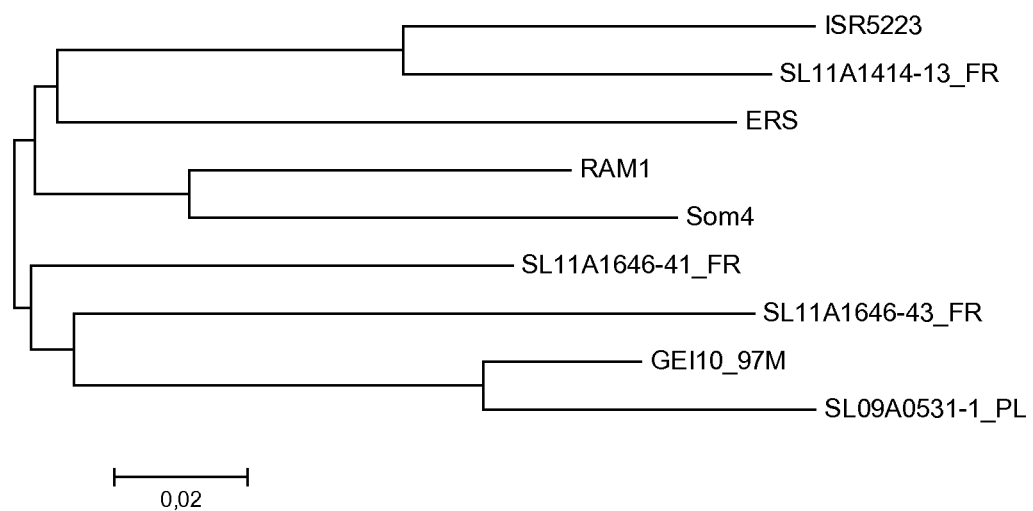

FIG. 1: Genotype subgroup 1 A
FIG. 2: Genotype subgroup 1 B
FIG. 3: Genotype group 2
FIG. 4: Genotype group 3
FIG. 5: Genotype group 4
FIG. 6: Genotype group 5

The invention claimed is:

1. A vaccine for reducing infection by avian Reovirus, the vaccine comprising an avian Reovirus antigenic material that is derived from avian Reoviruses from more than a single genotype group, and a pharmaceutically acceptable carrier, wherein the avian Reovirus antigenic material consists of antigenic material derived from a replicative form of an avian Reovirus from genotype group 1 and from a replicative form of an avian Reovirus from genotype group 4;
   wherein the avian Reovirus antigenic material comprises inactivated avian Reovirus;
   wherein the avian Reovirus from genotype group 1 comprises genetic information encoding a sigmaC protein comprising an amino acid sequence that has at least 85% amino acid sequence identity with the amino acid sequence of SEQ ID NO: 1; and
   wherein the avian Reovirus from genotype group 4 comprises genetic information encoding a sigmaC protein comprising an amino acid sequence that has at least 85% amino acid sequence identity with the amino acid sequence of SEQ ID NO: 4.

2. The vaccine of claim 1, wherein the antigenic material derived from avian Reovirus from genotype group 1, is derived from avian Reovirus from genotype subgroup 1B; wherein the avian Reovirus from genotype group 1B comprises genetic information encoding a sigmaC protein comprising an amino acid sequence that has at least 90% amino acid sequence identity with the amino acid sequence of SEQ ID NO: 1.

3. The vaccine of claim 1, wherein the vaccine comprises an adjuvant.

4. The vaccine of claim 1, wherein the vaccine comprises additional antigenic material that is derived from a microorganism pathogenic to an avian, but not from an avian Reovirus.

5. The vaccine of claim 1, wherein the step of inactivating both the avian Reovirus from genotype group 1 and the avian Reovirus from genotype group 4 is performed by an inactivation method selected from the group consisting of heat, radiation, formalin, beta-propiolactone, binary ethyleneimine, and beta-ethanolamine.

6. The vaccine of claim 5, wherein the vaccine comprises additional antigenic material that is derived from a microorganism pathogenic to an avian, but not from an avian Reovirus.

7. A method for the preparation of the vaccine of claim 1, comprising the step of inactivating both the avian Reovirus from genotype group 1 and the avian Reovirus from genotype group 4 by a method selected from the group consisting of heat, radiation, formalin, beta-propiolactone, binary ethyleneimine, and beta-ethanolamine.

8. A method for the preparation of the vaccine of claim 1, comprising the step of admixing the avian Reovirus antigenic material with an adjuvant.

9. A method for reducing infection by avian Reovirus in an avian, comprising administering the vaccine of claim 1 to the avian.

* * * * *